United States Patent
Lim et al.

(10) Patent No.: US 9,880,137 B2
(45) Date of Patent: Jan. 30, 2018

(54) COLORIMETRIC SENSOR ARRAYS BASED ON NANOPOROUS PIGMENTS

(75) Inventors: Sung H. Lim, Mountain View, CA (US); Christopher J. Musto, Champaign, IL (US); Liang Feng, Urbana, IL (US); Jonathan W. Kemling, Urbana, IL (US); Kenneth S. Suslick, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 1562 days.

(21) Appl. No.: 12/552,899

(22) Filed: Sep. 2, 2009

(65) Prior Publication Data

US 2010/0166604 A1    Jul. 1, 2010

Related U.S. Application Data

(60) Provisional application No. 61/094,301, filed on Sep. 4, 2008.

(51) Int. Cl.
| G01N 21/77 | (2006.01) |
| G01N 31/22 | (2006.01) |
| G01N 21/25 | (2006.01) |
| G01N 21/78 | (2006.01) |

(52) U.S. Cl.
CPC ........... *G01N 31/22* (2013.01); *G01N 21/253* (2013.01); *G01N 21/78* (2013.01)

(58) Field of Classification Search
CPC ..................................................... G01N 21/77
See application file for complete search history.

(56) References Cited

U.S. PATENT DOCUMENTS

| 4,739,645 | A  | 4/1988  | Drbal |
| 5,091,642 | A  | 2/1992  | Chow et al. |
| 5,817,475 | A  | 10/1998 | Gibbs et al. |
| 6,103,217 | A  | 8/2000  | Charych |
| 6,123,820 | A  | 9/2000  | Bergkuist et al. |
| 6,183,772 | B1 | 2/2001  | Charych et al. |
| 6,251,342 | B1 | 6/2001  | Narula et al. |
| 6,277,652 | B1 | 8/2001  | Jo et al. |
| 6,290,838 | B1 | 9/2001  | Mifsud et al. |
| 6,306,598 | B1 | 10/2001 | Charych et al. |
| 6,368,558 | B1 | 4/2002  | Suslick et al. |
| 6,495,102 | B1 | 12/2002 | Suslick et al. |
| 6,512,580 | B1 | 1/2003  | Behringer et al. |
| 6,541,270 | B2 | 4/2003  | Singh et al. |
| 6,562,424 | B1 | 5/2003  | Reisfeld et al. |
| 6,576,474 | B2 | 6/2003  | Wallach |
| 6,589,779 | B1 | 7/2003  | McDevitt et al. |
| 6,602,702 | B1 | 8/2003  | McDevitt et al. |
| 6,649,403 | B1 | 11/2003 | McDevitt et al. |
| 6,673,630 | B2 | 1/2004  | Albarella et al. |
| 6,680,206 | B1 | 1/2004  | McDevitt et al. |
| 6,689,620 | B1 | 2/2004  | Singh et al. |
| 6,713,298 | B2 | 3/2004  | McDevitt et al. |
| 6,908,770 | B1 | 6/2005  | McDevitt et al. |
| 6,919,201 | B2 | 7/2005  | Tanaami et al. |
| 7,022,517 | B1 | 4/2006  | McDevitt et al. |
| 7,101,660 | B2 | 9/2006  | Cunningham et al. |
| 7,261,857 | B2 | 8/2007  | Suslick et al. |
| 7,277,019 | B2 | 10/2007 | Povenmire |
| 7,316,899 | B2 | 1/2008  | McDevitt et al. |
| 7,364,918 | B2 | 4/2008  | Prince et al. |
| 2002/0115224 | A1 | 8/2002 | Rudel et al. |
| 2003/0012693 | A1 | 1/2003 | Otillar et al. |
| 2003/0129085 | A1 | 7/2003 | Suslick et al. |
| 2003/0143112 | A1 | 7/2003 | Suslick et al. |
| 2003/0166298 | A1 | 9/2003 | Suslick |
| 2004/0126897 | A1 | 7/2004 | Prince et al. |
| 2004/0157281 | A1 | 8/2004 | Hulkower et al. |
| 2004/0258759 | A1 | 12/2004 | Suslick et al. |
| 2004/0258762 | A1 | 12/2004 | Boppart et al. |
| 2005/0136548 | A1 | 6/2005 | McDevitt et al. |
| 2005/0171449 | A1 | 8/2005 | Suslick et al. |
| 2006/0029522 | A1 | 2/2006 | Theil |
| 2006/0051826 | A1 | 3/2006 | Tran-Thi et al. |
| 2006/0134796 | A1 | 6/2006 | Bommarito et al. |
| 2006/0228256 | A1 | 10/2006 | McDevitt et al. |
| 2008/0050839 | A1 | 2/2008 | Suslick et al. |

(Continued)

FOREIGN PATENT DOCUMENTS

| WO | 2004/077035 | 9/2004 |
| WO | WO 2004077035 A1 * | 9/2004 |
| WO | 2008/148987 | 12/2008 |

OTHER PUBLICATIONS

K. S. Suslick et al., Chemsensing: A Colorimetric Array Detector, 2 Proc. ISOEN 46-52 (2003).*
Suslick, K.S. et al., "Chemsensing: A Colorimetric Array Detector", Proceedings of the International Society of Olfaction & Electronic Noses 02, ed. A D'Amico and C. DiNatale; IEEE: Baltimore, pp. 46-52, (2003).
Albert, K.J. et al., "Cross-Reactive Chemical Sensor Arrays", Chem. Rev., 100, pp. 2595-2626, (2000).
Lewis, N.S., "Comparisons between Mammalian and Artificial Olfaction Based on Arrays of Carbon Black-Polymer Composite Vapor Detectors", Acc. Chem. Res. 37, pp. 663-672, (2004).
Johnson, B.A. et al., "Chemotopic Odorant Coding in a Mammalian Olfactory System", J. of Comparative Neurology, 503, pp. 1-34, (2007).
Anslyn, E.V., "Supramolecular Analytical Chemistry", J. Org. Chem., 72, pp. 687-699, (2007).

(Continued)

*Primary Examiner* — Randy Boyer
(74) *Attorney, Agent, or Firm* — Klintworth & Rozenblat IP LLP

(57) ABSTRACT

A colorimetric array includes a substrate, a first spot on the substrate, and a second spot on the substrate. The first spot includes a first nanoporous pigment that includes a first nanoporous material and a first immobilized, chemoresponsive colorant. The second spot includes a second nanoporous pigment that includes a second nanoporous material and a second immobilized, chemoresponsive colorant. The first nanoporous pigment is different from the second nanoporous pigment.

29 Claims, 8 Drawing Sheets

(56) References Cited

U.S. PATENT DOCUMENTS

2009/0112075 A1* 4/2009 Klok ............... A61B 5/0031
600/365

OTHER PUBLICATIONS

Anand, V, et al., "The latest trends in the taste assessment of pharmaceuticals", Drug Discovery Today, vol. 12, N. 5/6, pp. 257-265, (2007).
Suslick, K.S. et al., "Seeing Smells: Development of an Optoelectronics Nose", Quim Nova, vol. 30, No. 3, pp. 677-681, (2007).
Suslick, K.S., "An optoelectronic Nose: 'Seeing' Smells by Means of Colorimetric Sensor Arrays", MRS Bulletin October, pp. 720-725 (2004).
Suslick, K.S. et al., "Colorimetric sensor arrays for molecular recognition", Tetrahedron, 60, pp. 11133-11138, (2004).
Wang, J. et al., "Is the olfactory receptor a metalloprotein", Proc. Natl. Acad. Sci., vol. 100, No. 6, pp. 3035-3039, (2003).
Rakow, N.A. et al., "A Colorimetric sensor array for odour visualization", Nature, vol. 406, pp. 710-713, (2000).
Rakow, N.A. et al., "Molecular recognition and discrimination of amines with a colorimetric array", Angew. Chem. Int. Ed., 44, pp. 4529-4532, (2005).
Janzen, M.C. et al., "Colorimetric Sensor Arrays for Volatile Organic Compounds", Analytical Chemistry, vol. 78, No. 11, pp. 3591-3600, (2006).
Zhang, C. et al., "A Colorimetric Sensor Array for Organics in Water", J. Am. Chem. Soc., 127, pp. 11548-11549, (2005).
Zhang, C. et al., "Colorimetric Sensor Arrays for the Analysis of Beers: A Feasibility Study", J. Agric. Food Chem., 54, pp. 4925-4931, (2006).
Zhang, C. et al., "Colorimetric Sensor Array for Soft Drink Analysis", J. Agric. Food Chem., 2007, 55, pp. 237-242, (2007).
Reisch, M.S., "Building a Better Nose", Chemical and Engineering News, vol. 86, No. 13, pp. 18-19, (2008).
Rök, F. et al., "Electronic Nose: Current Status and Future Trends", Chem. Rev., 108, pp. 705-725, (2008).
Zaggout, F.R., "Encapsulation of Bromocresol Green pH Indicator into a Sol-Gel Matrix", J. Dispersion Science and Technology, 26, pp. 757-761, (2005).
Rottman, C. et al., "Doped sol-gel glasses as pH sensors", Materials Letters, 13, pp. 293-298, (1992).
Zusman, R. et al., "Doped sol-gel glasses as chemical sensors" Journal of Non-Crystalline Solids, 122, pp. 107-109, (1990).
Kowada, Y. et al., "Preparation of Silica-Gel Film with pH Indicators by the Sol-Gel Method", Journal of Sol-Gel Science and Technology, 33, pp. 175-185, (2005).
Zaggout, F.R. et al., "Behavior of thymol blue analytical pH-indicator entrapped into sol-gel matrix", Materials Letters, 60, pp. 3463-3467, (2006).
Villegas, M.A. et al., "Sol-gel silica coatings doped with a pH-sensitive chromophore", Thin Solid Films, 351, pp. 103-108, (1999).
Murphy, C.J. et al., "Chemical sensing and imaginh with metallic nanorods", Chemical Communications, pp. 544-557, (2008).
Suslick, K.S. et al., "Microporous Porphyrin Solids", Accounts of Chemical Research, vol. 38, No. 4, pp. 283-291, (2005).
Lee, J.W. et al., "Colorimetric Identification of Carbohydrates by a pH Indicator/pH Change Inducer Ensemble", Angew. Chem., Int. Ed. Engl., 45, pp. 6485-6487, (2006).
Dowlut, M. et al., "An Improved Class of Sugar-Binding Boronic Acids, Soluble and Capable of Complexing Glycosides in Neutral Water"; J. Am. Chem. Soc., 128, pp. 4226-4227, (2006).
Yan, J. et al., "The relationship among $pK_a$, pH, and binding constants in the interactions between boronic acids and diols—it is not as simple as it appears", Tetrahedron, 60, pp. 11205-11209, (2004).
James, T.D. et al., "Saccharide Sensing with Molecular Receptors Based on Boronic Acid", Angew. Chem., Int. Ed. Engl., 35, pp. 1911-1922, (1996).
Sen, A. et al., "Shape-Selective Discrimination of Small Organic Molecules", J. Am. Chem. Soc., 122, pp. 11565-11566, (2000).
Suslick, K. S. et al., "A Colorimetric Nose: 'Smell-Seeing'" Artificial Chemical Sensing: Olfaction and the Electronic Nose, Electrochem. Soc., Pennington, NJ, pp. 8-14, (2001).
Zhang, C. et al., "Syntheses of Boronic-Acid-Appended Metalloporphyrins as Potential Colorimetric Sensors for Sugars and Carbohydrates." J. Porphyrins & Phthalocyanines, 9, pp. 659-666, (2005).
Rakow, N.A. et al., "Molecular Recognition and Discrimination of Amines with a Colorimetric Array" Angew. Chem., 117, pp. 4604-4608, (2005).
Rottman, C. et al., "Sol-gel physical and covalent entrapment of three methyl red indicators: a comparative study", Journal of Sol-Gel Science and Technology, 13, pp. 17-25, (1998).
Malins, C. et al., "Influence of the surface polarity of dye-doped sol-gel glass films on optical ammonia sensor response", Thin Solid Films, 368, pp. 105-110, (2000).
Malins, C. et al., "Sol-gel immobilized ruthenium(II) polypyridyl complexes as chemical transducers for optical pH sensing", Sensors and Actuators, B, B67, pp. 89-95, (2000).
Malins, C. et al., "Multi-analyte optical chemical sensor employing a plastic substrate", Measurement Science and Technology, 11, pp. 1105-1110, (2000).
Rottman, C. et al., Effects of water/silane r-ratio and humidity on properties of sol-gel-entrapped indicators. Proceedings of SPIE, vol. 3943, pp. 154-162, (2000).
Villegas, M.A. et al., "Chemical and optical properties of dye-doped sol-gel films", Journal of Materials Science, 35, pp. 4615-4619, (2000).
Villegas, M.A. et al., "Eriochrome cyanine doped-sol-gel coatings. Optical behavior against pH", Journal of the European Ceramic Society 2000, 20, pp. 1621-1628, (2000).
Onida, B. et al., "Synthesis and characterization of dye-containing MCM-41 materials", Studies in Surface Science and Catalysis, 140, pp. 361-368, (2001).
Onida, B. et al., "Accessibility of dye-molecules embedded in the micellar phase of hybrid mesostructured MCM41-type materials", Studies in Surface and Catalysis, 156, pp. 379-382, (2003).
Onida, B. et al., "A NH3-responding material based on reichardt's dye-impregnated mesoporous silica", Studies in Surface Science and Catalysis, 146, pp. 453-456, (2003).
Borello, L. et al., "Accessibility of dye molecules embedded in surfactant-silica hybrid materials in both powder and film forms", Sensors and Actuators, B: 100, pp. 107-111, (2004).
Fiorilli, S. et al., "Mesoporous SBA-15 silica impregnated with Reichardt's dye: a material optically responding to NH3", Sensors and Actuators, B 100, pp. 103-106, (2004).
Onida, B. et al., "Accessibility to gases of dye molecules in hybrid surfactant-silica mesophases", Studies in Surfaces Science and Catalysis, vol. 154, pp. 3010-3016, (2004).
Onida, B. et al., "Mechanism of the Optical Response of Mesoporous Silica Impregnated with Reichardt's Dye to NH3 and Other Gases", Journal of Physical Chemistry B 2004, 108, pp. 16617-16620, (2004).
Bodoardo, S. et al., "Methylene blue encapsulated in silica-based mesophases: characterization and electrochemical activity", Microporous and Mesoporous Materials, 79, (1-3), pp. 275-281 (2005).
Zagogut, F.R. et al., "Encapsulation of methyl orange pH-indicator into a sol-gel matrix", Materials Letters, 59, pp. 2928-2931, (2005).
Zaggout, F.R. et al., "Encapsulation methyl red pH-indicator into a sol-gel matrix", Journal of Dispersion Science and Technology, vol. 26, No. 5, pp. 518-522, (2005).
Oberg, K.I. et al., "Simple optical sensor for amine vapors based on dyed silica microspheres", Sensors and Actuators, B Chemical B115, pp. 79-85 (2006).
Wu, Z. et al., "Understanding the mechanisms of reaction and release of acid-base indicators entrapped in hybrid gels", Journal of Non-Crystalline Soldis, 352, pp. 5498-5007, (2006).
Zaggout, F.R. et al., "Entrapment of phenol red pH indicator into a sol gel matrix", Materials Letters, 60, pp. 1026-1030, (2006).

(56) References Cited

OTHER PUBLICATIONS

Zaggout F.R. et al., "Spectrophotometric studies of entrapped thymol phtalein pH indicator into sol-gel matrix", Journal of Dispersion Science and Technology, vol. 27, issue 7, pp. 1003-1007, (2006).
Suslick, K.S., "Shape Selective Oxidation by Metalloporphyrins", The Porphyrin Handbook, Kadish, K.; Smith, K.; Guilard, R., ed.; Academic Press: New York, Biochemistry and Binding: Activation of Small Molecules, vol. 4, ch. 28, pp. 41-63, (2000).
Bhyrappa, P. et al., "Shape Selective Ligation to Dendrimer-Metalloporphyrins", Journal of the American Chemical Society, vol. 121, No. 1, pp. 262-263, (1999).
Zarzo, M., "The sense of smell: molecular basis of odorant recognition", Biol. Rev., 82, pp. 455-479, (2007).
Hierlemann, A. et al., "Higher-order chemical sensing", Chem. Rev., 108, pp. 563-613 (2008).
Walt, D. R. "Electronic noses: wake up and smell the coffee", Anal. Chem. p. 45A, (2005).
Wolfbeis, O.S., "Materials for fluorescence-based optical chemical sensors", J. Mater. Chem., 15, pp. 2657-2669, (2005).
Hsieh, M-D. et al., "Limits of recognition for simple vapor mixtures determined with microsensor array", Anal. Chem., 76, pp. 1885-1895, (2004).
Janata, J. et al., "Conducting polymers in electronic chemical sensors", Nat. Mater. 2, pp. 19-24, (2003).
Grate, J.W., "Acoustic wave microsensor arrays for vapor sensing", Chem. Rev, pp. 2627-2647, (2000).
Lim, S. et al., "A colorimetric sensor array for detection and identification of sugars", Org. Lett. 10, pp. 4405-4408, (2008).
Bang, J. H. et al., "Chemically responsive nanoporous pigments: colorimetric sensor arrays and the identification of aliphatic amines", Langmuir, 24, pp. 13168-13172, (2008).
Musto, C.J. et al., "Colorimetric detection and identification of natural and artifical sweeteners", Analytical Chemistry, vol. 81, No. 15, pp. 6526-6533, (2009).
Dunbar, R.A. et al., "Development of chemical sensing platforms based on sol-gel-derived thin films: origin of film age vs. performance trade-offs", Analytical Chemistry, vol. 68, pp. 604-610 (1996).
Jeronimo, P.C.A. et al., "Optical sensors and biosensors based on sol-gel films", Talanta, 72, pp. 13-27, (2007).
Rottman, C. et al., "Surfactant-induced modification of dopants reactivity in sol-gel matrixes", J. Am. Chem., Soc. 121, pp. 8533-8543, (1999).
Steumpfle, A.K. et al., "Final Report of International Task Force-25: Hazard From Toxic Industrial Chemicals" US GPO: Washington, DC. <http://file.sunshinepress.org:54445/us-uk-ca-mou-itf25-1996.pdf>, pp. 1-28, (1996).
Armour, S. J. et al. International Task Force 40: Toxic Industrial Chemicals (TICs)—Operational and Medical Concerns, <http://chppm-www.apgea.army.mil/desp/pages/jeswg/4QFY01/itf-40-2-US.ppt>, pp. 1-15, (2001).
Hill, H.H. et al., "Conventional analytical methods for chemical warfare agents", Pure Appl. Chem., 74, pp. 2281-2291 (2002).
Hammond, M.H. et al., "A novel chemical detector using cermet sensors and pattern recognition methods for toxic industrial chemicals", Sensor and Actuators B Chemical, B116, pp. 135-144, (2006).
Meier, D.C. et al., "The potential for and challenges of detecting chemical hazards with temperature-programmed microsensors", Sensors and Actuators B Chemical, B121, pp. 282-294, (2007).
Scott, S.M. et al., "Data analysis for electronic nose systems", Microchim. Acta, 156, pp. 183-207, (2007).
Lange, U. et al., "Conducting polymers in chemical sensors and arrays", Analytica Chimica Acta, 614, pp. 1-26, (2008).
Wolfrum, E.J. et al., "Metal oxide sensor sensor arrays for the detection, differentiation, and quantification of volatile organic compounds at sub-parts-per-million concentration levels", Sensors and Actuators B, 115, pp. 322-329, (2006).

Klotz, M. et al., "Tailoring of the Porosity in Sol-Gen Derived Silica Thin Layers", Bull. Korean Chemical Society, vol. 20, No. 8, pp. 879-884, (1999).
MacCraith, B.D. et al., "Optical Chemical Sensors Based on Sol-Gel Materials: Recent Advances and Critical Issues", J. Sol-Gel Sci. Technol., 8, pp. 1053-1061, (1997).
McDonagh, C. et al.; "Tailoring of Sol-Gel Films for Optical Sensing of Oxygen in Gas and Aqueous Phases", Anal. Chem., 70, pp. 45-50, (1998).
Sanchez-Barragan, I. et al., "Tailoring the pH response range of fluorescent-based pH sensing phases by sol-gel surfactants co-immobilization", Sensors and Actuators B, 107, pp. 69-76, (2005).
Ruprecht, W., "The historical development of the consumption of sweeteners—a learning approach", J. Evol. Econ. 15, pp. 247-272, (2005).
Mattes, R.D. et al., "Nonnutritive sweetener consumption in humans: effects on appetite and food intake and their putative mechanisms", American Journal of Clinical Nutrition, 89, pp. 1-14, (2009).
Heller, L., "Sugar demand rising at expense of sweeteners, claims sugar industry", http://www.foodnavigator-usa.com/Financial-Industry/Sugar-demand-rising-at-expense-of-sweeteners-claims-sugar-industry, (2005).
Prance, L., "Obesity concerns drive artificial sweetener market", http://www.foodnavigator-usa.com/Financial-Industry/Obesity-concerns-drive-artificial-sweetener-market, (2007).
Buchgraber, M. et al., "Determination of Nine Intense Sweeteners in Foodstuffs by High-Performance Liquid Chromatography and Evaporative Light-Scattering Detection: Interlaboratory Study", Journal of AOAC International, 92, pp. 208-222, (2009).
Filho, J.C. et al., "Potentiometric determination of saccharin in commercial artificial sweeteners using a silver electrode", Food Chem., 83, pp. 297-301, (2003).
Chen, Q.-C. et al., "Separation and determination of four artificial sweeteners and citric acid by high-performance anion-exchange chromatography", J. of Chromatography A, 771, pp. 135-143, (1997).
Chen, Q.-C. et al., "Simultaneous determination of artifical sweeteners, preservatives, caffeine, theobromine and theophylline in food and pharmaceutical preparations by ion chromatography", J. of Chromatography A, 937, pp. 57-64, (2001).
Galletti, G.C. et al., "Analysis of the Artificial Sweetener Aspartame by Means of Liquid Chromatorgraphy/Electrospray Mass Spectrometry", Rapid Communications in Mass Spectrometry, 10, pp. 1153-1155, (1996).
James, T.D., "Novel fluorescence sensor for 'small' saccharides", Chem Commun., pp. 71-72 (1997).
Qu, F. et al., "Determination of aspartame by ion chromatography with electrochemical integrated amperometric detection", J. Chromatogr. A, 850, pp. 277-284, (1999).
Wasik, A. et al., "Simultaneous determination of nine intense sweeteners in foodstuffs by high performance liquid chromatography and evaporative light scattering detection—Development and single-laboratroy validation", J. Chromatography A, 1157, pp. 187-196, (2007).
Zhao, J. et al., "Chemoselective and enantioselective fluorescent recognition of sugar alcohols by a bisboronic acid receptor", Journal of Material Chemistry, vol. 15, pp. 2896-2901, (2005).
Zhu, Y. et al., "Separation and simultaneous determination of four artificial sweeteners in food and beverages by ion chromatography", Journal of Chromatography A, 1085, pp. 143-146, (2005).
Yang, D-J. et al., "Simultaneous Determination of Nonnutritive Sweeteners in Foods by HPLC/ESI-MS", Journal of Agricultural and Food Chemistry, 57, pp. 3022-3027, (2009).
Wang, W. et al., "Boronic Acid-Based Sensors", Current Organic Chemistry, 6, pp. 1285-1317, (2002).
Springsteen, G. et al., "A detailed examination of boronic acid-diol complexation", Tetrahedron, 58, pp. 5291-5300, (2002).
Mulla, H.R. et al., 3-Methoxycarbonyl-5-nitrophenyl boronic acid: high affinity diol recognition at neutral pH, Bioorganic & Medicinal Chem. Letters, 14, pp. 25-27, (2004).
Ni, W. et al., "The Design of Boronic Acid Spectroscopic Reporter Compounds by Taking Advantabe of the $pK_a$-Lowering Effect of

(56) References Cited

OTHER PUBLICATIONS

Diol Binding: Nitrophenol-Based Color Reporters for Diols", J. Org. Chem., 69, pp. 1999-2007, (2004).

Boduroglu, S. et al., "A colorimetric titration method for quantification of millimolar glucose in a pH 7.4 aqueous phosphate buffer", Bioorganic & Medicincal Chemistry Letters, 15, pp. 3974-3977, (2005).

Edwards, N.Y. et al., "Boronic Acid Based Peptidic Receptors for Pattern-Based Saccharide Sensing in Neutral Aqueous Media, an Application in Real-Life Samples", Journal of the American Chemical Society, vol. 129, pp. 13575-13583, (2007).

Kim, Y.H. et al., "Sugar sensing base on induced pH changes", Chem. Commun., pp. 2299-2301, (2007).

Schiller, A. et al., "A Fluorescent Sensor Array for Saccharides Based on Boronic Acid Appended Bipyridinium Salts", Angewandte Chemie Int. Ed., 46, pp. 6457-6459, (2007).

Zhang, T. et al., "A Colorimetric Boronic Acid Based Sensing Ensemble for Carboxy and Phospho Sugars", Organic Letters, vol. 8, No. 8, pp. 1649-1652, (2006).

International Search Report dated Jan. 19, 2010 for PCT application No. PCT/US2009/055748.

Lim, S.H. et al., "An optoelectronic nose for the detection of toxic gases", Nature Chemistry, vol. 1, pp. 562-567, (2009).

Lim, S.H. et al., "An optoelectonic nose for the detection of toxic gases", Nature Chemistry, Supplementary Information, pp. 1-19, (2009).

Musto, C.J. et al., "Supporting information for detection and identification of natural and artificial sweeteners using a colorimetric sensor array", Department of Chemistry, University of Illinois, pp. S1-S6, (2009).

Lim, S.H. et al., "Supporting information a colorimetric sensor array for detection and identification of sugars", Department of Chemistry, University of Illinois, pp. S1-S6, (2008).

Suslick, K.S. et al., "Smellseeing: A Colorimetric electronic nose", 9$^{th}$ International Symposium on Olfaction and Electronic Nose, Rome, pp. 27-28, Sep. 30-Oct. 2, 2002.

\* cited by examiner

COLORIMETRIC SENSOR ARRAYS BASED ON NANOPOROUS PIGMENTS

CROSS REFERENCE TO RELATED APPLICATION

This application claims the benefit of provisional application No. 61/094,301 entitled "Colorimetric Sensor Arrays Based on Nanoporous Pigments" filed 4 Sep. 2008, the entire contents of which are hereby incorporated by reference, except where inconsistent with the present application.

FEDERALLY SPONSORED RESEARCH OR DEVELOPMENT

The subject matter of this application may in part have been funded by the National Science Foundation (BES 05-28499) and Department of Defense (ArmyW91CRB-06-C-0018). The government may have certain rights in this invention.

BACKGROUND

Array based sensing has emerged as a powerful tool for the detection of chemically diverse analytes. These systems mimic the mammalian gustatory and olfactory systems by producing specificity, not from any single sensor, but as a unique composite response for each analyte. Such cross-reactive sensor arrays have application both as electronic nose technology for the detection of volatiles and gases [1-5], and as electronic tongue technology for the detection of aqueous analytes [6-7].

Conventional sensor arrays typically have been based on a variety of changes in the properties of individual sensors. For example, absorption of the analyte into conductive polymers or polymer composites can change the electrical properties of the polymers or composites. In another example, adsorption of the analyte onto surfaces such as metal oxide surfaces can provide for combustion reactions, oxidation reactions or other electrochemical processes, which can be electrically detected. In yet another example, a single fluorophore can be included in an array of different adsorbent polymers, and the change in composite fluorescence of the array can be measured.

Using a different approach from these conventional sensor arrays, colorimetric sensor arrays are based on optoelectronics. A colorimetric sensor is a sensor that includes one or more materials that undergo a change in spectral properties upon exposure to an appropriate change in the environment of the sensor. The change in spectral properties may include a change in the absorbance, fluorescence and/or phosphorescence of electromagnetic radiation, including ultraviolet, visible and/or infrared radiation.

Colorimetric sensor arrays typically include an array of cross-reactive chemoresponsive dyes, where the colors of the chemoresponsive dyes are affected by a wide range of analyte-dye interactions. Colorimetric arrays have been used for the identification and quantification of a wide range of analytes, both in the gas phase and in aqueous solutions [8-17]. The arrays typically are made simply by printing the hydrophobic chemoresponsive dyes onto a hydrophobic membrane.

The chemoresponsive dyes used in colorimetric sensor arrays typically have been limited to soluble molecular dyes, which are present in a porous film [18-23]. Insoluble, nonporous pigments have not provided sufficient contact between the analyte and the chromophores of the pigment, since the chromophores at the surface of the pigment are a small fraction of the total number of chromophores. Likewise, nonporous films have not provided sufficient contact between a dye in the film and the analyte in the sample.

There are a variety of drawbacks to the use of soluble molecular dyes in porous films for colorimetric sensor arrays. Aggressive solvents, such as halocarbons or aromatics, are typically used for printing the dyes. The dyes can leach into analyte solutions from the porous film. The dyes may be unstable, leading to a limited shelf-life. Crystallization of the dyes after printing on the membrane can render the dyes inactive.

One approach to addressing these drawbacks has been to immobilize the chemoresponsive dyes in sol-gel matrices [24-29]. These sol-gel matrices, however, have had poor adherence to the hydrophobic surfaces used for sensor arrays. Thus, the sol-gel based dyes typically have been prepared as a film or a monolithic disk, and have been used individually rather than as an array with other chemoresponsive dyes.

It would be desirable to provide a colorimetric sensor array having increased stability relative to conventional colorimetric arrays, and that does not undergo leaching of soluble dyes during use. Ideally, such a sensor array would include a variety of different chemoresponsive colorants, including dyes and pigments. It would also be desirable for such an array to be formed by a method that does not include aggressive solvents, and that is compatible with reproducible, high-throughput fabrication.

SUMMARY

In one aspect, the invention provides a colorimetric array including a substrate, a first spot on the substrate, and a second spot on the substrate. The first spot includes a first nanoporous pigment that includes a first nanoporous material and a first immobilized, chemoresponsive colorant. The second spot includes a second nanoporous pigment that includes a second nanoporous material and a second immobilized, chemoresponsive colorant. The first nanoporous pigment is different from the second nanoporous pigment.

In another aspect, the invention provides a method of making a colorimetric array including depositing a first liquid at a first point on a substrate, depositing a second liquid at a second point on a substrate, converting the first liquid into a first spot on the substrate, and converting the second liquid into a second spot on the substrate. The first spot includes a first nanoporous pigment including a first nanoporous material and a first immobilized, chemoresponsive colorant. The second spot includes a second nanoporous pigment including a second nanoporous material and a second immobilized, chemoresponsive colorant. The first nanoporous pigment is different from the second nanoporous pigment.

These aspects may include a method of making a colorimetric array in which the first liquid includes a first nanoporous material precursor and a first chemoresponsive colorant, and the converting the first liquid into a first spot includes solidifying the first nanoporous material precursor to form the first nanoporous material. These aspects may include a method of making a colorimetric array in which the first liquid includes a first colloidal suspension including a first solvent and particles of the first nanoporous pigment, and the converting the first liquid into a first spot includes drying the first colloidal suspension.

In yet another aspect, the invention provides a method of detecting an analyte in a sample, including obtaining a first image of the colorimetric array in the absence of the analyte, obtaining a second image of the colorimetric array in the presence of the sample, and analyzing a difference between the first image and the second image.

The following definitions are included to provide a clear and consistent understanding of the specification and claims.

The term "colorant" means any material that absorbs light and/or that emits light when exposed to higher frequency electromagnetic radiation. A light-absorbing portion of a colorant is referred to as a chromophore, and a light-emitting portion of a colorant is referred to as a fluorophore.

The term "chemoresponsive colorant" means a colorant that undergoes a change in spectral properties in response to an appropriate change in its chemical environment.

The term "change in spectral properties" of a colorant means a change in the frequency and/or intensity of the light the colorant absorbs and/or emits.

The term "dye" means a soluble colorant.

The term "pigment" means an insoluble colorant.

The term "nanoparticle" means a particle with one or more dimensions of 100 nanometers (nm) or less.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1:
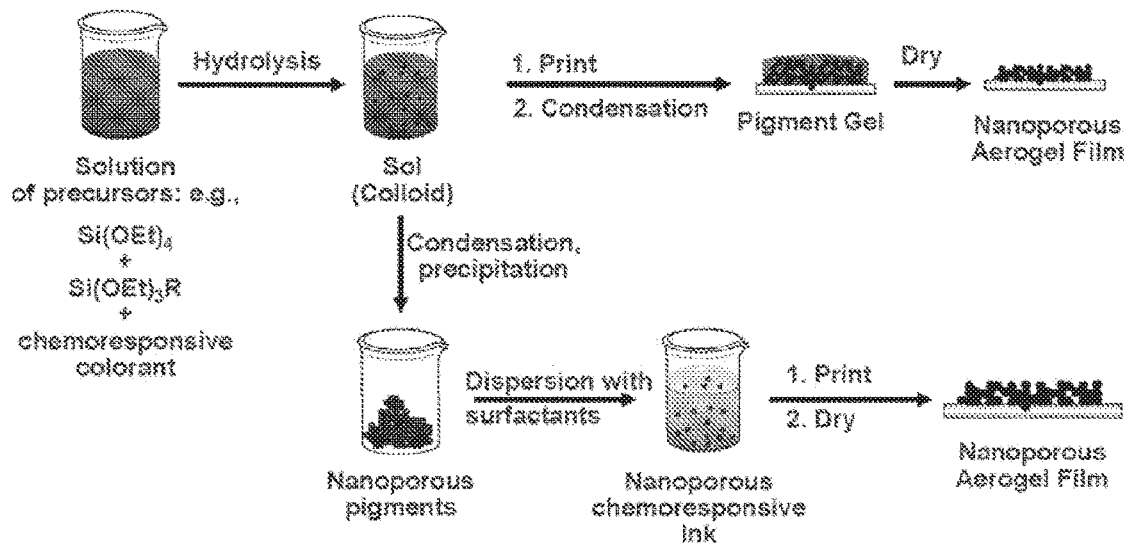
FIG. 1 is a schematic diagram of examples of two methods of making a calorimetric array.

The present invention is based on the discovery that colorimetric arrays that include nanoporous pigments can have increased stability relative to conventional colorimetric arrays. Sensors including a colorimetric array that includes nanoporous pigments also may have improved sensitivity and selectivity toward analytes than conventional colorimetric arrays. In addition, the arrays including nanoporous pigments can provide a number of processing advantages.

A colorimetric array includes a substrate, a first spot on the substrate, and a second spot on the substrate. The first spot includes a first nanoporous pigment including a first nanoporous material and a first immobilized, chemoresponsive colorant. The second spot includes a second nanoporous pigment including a second nanoporous material and a second immobilized, chemoresponsive colorant. The second nanoporous pigment is different from the first nanoporous pigment.

The substrate may be any material that can retain a spot on its surface. Examples of substrates include polymeric membranes, such as cellulose acetate or polyvinylidene difluoride (PVDF). Examples of substrates include nonporous surfaces such as glass, metal, or a nonporous polymer surface such as poly(tetrafluoroethylene) (PTFE) or poly (ethylene terephthalate) (PET).

The first nanoporous pigment includes a first nanoporous material and a first immobilized, chemoresponsive colorant, and the second nanoporous pigment includes a second nanoporous material and a second immobilized, chemoresponsive colorant. The first and second nanoporous materials may be the same, or they may be different. The first and second immobilized, chemoresponsive colorants also may be the same, or may be different. In order for the first and second nanoporous pigments to be different, at least one of the nanoporous materials and the immobilized, chemoresponsive colorants must be different between the two spots. If the first and second nanoporous materials are the same, then the first and second immobilized, chemoresponsive colorants are different. If the first and second immobilized, chemoresponsive colorants are the same, then the first and second nanoporous materials are different. In one example, the first and second nanoporous materials are different, and the first and second immobilized, chemoresponsive colorants also are different.

The nanoporous material may be any material that includes pores, reticulations or void spaces with dimensions from 0.2 to 1000 nm. Preferably the nanoporous material includes pores with dimensions from 0.5 to 100 nm. Preferably the nanoporous material includes pores that are interconnected, such that a fluid can flow between the pores of the material. A nanoporous material may be, for example, an inorganic network, such as a porous ceramic or a zeolite. A nanoporous material may be, for example, an organic network, such as a collection of carbon tubes or a cross-linked gel. A nanoporous material may be, for example, a membrane material, such as a microfiltration membrane or an ultrafiltration membrane. A nanoporous material may be a combination of an inorganic network, an organic network and/or a membrane, such as an inorganic/organic composite.

The immobilized, chemoresponsive colorant may be any chemoresponsive colorant that is immobilized as a part of a nanoporous pigment. A colorant is immobilized as a part of a nanoporous pigment if less than 1% of the colorant is extracted from the nanoporous pigment when in contact with a volume of water equal to or greater than the volume of the nanoporous pigment, for a period of 1 hour at room temperature.

The chemoresponsive colorant may be a chemoresponsive dye that is insolubilized by the nanoporous material. Examples of chemoresponsive dyes include Lewis acid-base dyes, structure-sensitive porphyrins, pH sensitive dyes, solvatochromic dyes, vapochromic dyes, redox sensitive dyes, and metal ion sensitive dyes. Chemoresponsive dyes may be responsive to one or more chemical interactions including Lewis acid-base interaction, Brønsted acid-base interaction, ligand binding, π-π complexation, hydrogen bonding, polarization, oxidation/reduction, and metal coordination.

The chemoresponsive dye may be insolubilized by the nanoporous material through a chemical bond, such as a covalent bond, an ionic bond or a hydrogen bond. The chemoresponsive dye may be insolubilized by the nanoporous material through adsorption on a surface of the nanoporous material. The chemoresponsive dye may be insolubilized by the nanoporous material through physical entrapment of the dye in the nanoporous material. The chemoresponsive dye may be on an exterior surface of the nanoporous material, or it may be on an interior surface, such as within the pores, reticulations or void spaces of the material.

The chemoresponsive dye may be, for example, a Lewis acid-base dye, such as a Lewis acid dye or a Lewis base dye. A Lewis acid-base dye is a dye that can interact with a substance by acceptor-donor sharing of a pair of electrons with the substance, resulting in a change in spectral properties. The change in spectral properties for a Lewis acid-base dye may be related to Lewis acid-base interaction and ligand binding, but also to π-π complexation, hydrogen bonding, and/or polarity changes. Lewis acid-base dyes include metal-ion containing dyes, such as metalloporphyrins and other metal ion ligating macrocycles or chelating dyes; boron- and boronic acid containing dyes; and dyes with accessible heteroatoms (e.g., N, O, S, P) with lone electron pairs capable of Lewis coordination (e.g., "complexometric dyes").

Examples of Lewis acid-base dyes include metal ion-containing dyes, such as metal ion-containing porphyrins (i.e., metalloporphyrins), salen complexes, chlorins, bispocket porphyrins, and phthalocyanines. Diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). In one example, a parent porphyrin is the so-called free base form 5,10,15,20-tetraphenylporphyrin ($H_2TPP$), its dianion is 5,10,15,20-tetraphenyl-porphyrinate(-2) (TPP dianion), its metalated complexes, and its acid forms ($H_3TPP^+$ and $H_4TPP^{+2}$). This porphyrin may form metalated complexes, for example, with $Sn^{4+}$, $Co^{3+}$, $Co^{2+}$, $Cr^{3+}$, $Mn^{3+}$, $Fe^{3+}$, $Cu^{2+}$, $Ru^{2+}$, $Zn^{2+}$, $Ag^{2+}$, $In^{3+}$, and $Ir^{3+}$. Metal ion-containing metalloporphyrin dyes are described, for example, in U.S. Pat. No. 6,368,558 B1 to Suslick et al. and in U.S. Patent Application Publication No. 2003/0143112 A1 to Suslick et al.

Visible spectral shifts and absorption intensity differences for metalloporphyrins may occur upon ligation of the metal center, leading to readily observable changes in spectral properties. The magnitude of this spectral shift typically correlates with the polarizability of the ligand, thus allowing for distinction between analytes based on the electronic properties of the analytes. Using metal centers that span a range of chemical hardness and ligand binding affinity, it may be possible to differentiate between a wide range of volatile analytes, including molecules having soft functional groups such as thiols, and molecules having hard functional groups such as amines. Because porphyrins can exhibit wavelength and intensity changes in their absorption bands with varying solvent polarity, an array that includes porphyrins may be used to colorimetrically distinguish among a series of weakly ligating solvent vapors, such as arenes, halocarbons and ketones.

The chemoresponsive dye may be, for example, a structure-sensitive porphyrin. Structure-sensitive porphyrins include modified porphyrins that include a super structure bonded to the periphery of the porphyrin. For example, metalloporphyrins functionalized with a super structure at the periphery may limit steric access to the metal ion, allowing for shape-selective distinction of analytes, such as between n-hexylamine and cyclohexylamine. Controlling the ligation of various nitrogenous ligands to dendrimer-metalloporphyrins can provide for selectivities over a range of more than $10^4$.

Examples of super structures that may be bonded to a porphyrin include dendrimers, siloxyl groups, aryl groups such as phenyl groups, alkyl groups such as t-butyl groups, organometallic groups, inorganic groups, and other bulky substituents. Porphyrins bearing super structures may be selective to molecular shape, including sensitivity to steric factors, enantiomeric factors, and regioisomeric factors. For example, the structures may provide sterically constrained pockets on one or both faces of the porphyrin. Porphyrins bearing super structures also may be sensitive to factors such as hydrogen bonding and acid-base functionalities. Metal ion-containing metalloporphyrin dyes that include a super structure bonded to the periphery of the porphyrin, and methods of making such dyes, are disclosed, for example, in U.S. Pat. No. 6,495,102 B1 to Suslick et al.

One example of modified porphyrins that include a super structure bonded to the periphery of the porphyrins is the family of tetrakis(2,4,6-trimethoxyphenyl)-porphyrin (TTMPP). By varying the metal in this porphyrin, it is possible to distinguish between substances such as between t-butylamine and n-butylamine, and between cyclohexylamine and n-hexylamine.

Another example of a modified porphyrin that includes a super structure bonded to the periphery of the porphyrin is the family of silylether-metalloporphyrins. For example, scaffolds derived from the reaction of 5,10,15,20-tetrakis(2',6'-dihydroxyphenyl)porphyrinatozinc(II) with t-butyldimethylsilyl chloride provide Zn(II) porphyrin having in which the two faces are protected with six, seven, or eight siloxyl groups. This can result in a set of three porphyrins having similar electronic properties, but having different hindrance around the central metal atom present in the porphyrin. The shape selectivities of these porphyrins may be up to $10^7$ or greater.

Other examples of a modified porphyrins that include a super structure bonded to the periphery of the porphyrin include siloxyl-substituted bis-pocket porphyrins, such as 5-phenyl-10,15,20-tris(2',6'-dihydroxyphenyl)porphyrinatozinc(II); 5,10,15,20-tetrakis(2',6'-dihydroxyphenyl)porphyrinatozinc(II); 5(phenyl)-10,15,20-trikis(2',6'-disilyloxyphenyl)porphyrinatozinc(II); 5,10,15-trikis(2',6'-disilyloxyphenyl)-20-(2'-hydroxy-6'-silyloxyphenyl)porphyrinatozinc(II). The shape selectivities of these porphyrins may be up to $10^7$ or greater compared to unhindered metalloporphyrins. Fine-tuning of ligation properties of these porphyrins may be possible, such as by using pockets of varying steric demands.

Other examples of metal ion-containing metalloporphyrin dyes that include a super structure bonded to the periphery of the porphyrin include 2,3,7,8,12,13,17,18-octafluoro-5,10,15,20-tetrakis(pentafluorophenyl)-porphyrinatocobalt (II); 2,3,7,8,12,13,17,18-octabromo-5,10,15,20-tetraphenyl-porphyrinatozinc (II); 5,10,15,20-tetraphenylporphyrinatozinc(II); 5(phenyl)-10,15,20-trikis (2',6'-bis(dimethyl-t-butylsiloxyl)phenyl)porphyrinatozinc (II); 5,10,15,20-tetrakis(2',6'-bis(dimethyl-t-butylsiloxyl) phenyl)porphyrinatozinc(II); 5,10,15,20-tetraphenylporphyrinatocobalt (II); 5,10,15,20-tetrakis(2,6-difluorophenyl)-porphyrinatozinc(II); and 5,10,15,20-tetrakis(2,4,6-trimethylphenyl)-porphyrinatozinc(II).

An array that includes a structure-sensitive porphyrin may be used in combinatorial libraries for shape selective detection of substrates. Such an array also may include a structure-sensitive having chiral super structures on the periphery of the porphyrin, which may provide for identification of chiral substrates, such as drugs, natural products and components of biological samples from a patient. Such an array also may be used for analysis of biological entities based on the surface proteins, oligosaccharides, antigens, etc., that interact with the metalloporphyrins. Examples of biological entities include individual species of bacteria and viruses. Such an array also may be used for analysis of nucleic acid sequences, including specific recognition of individual sequences of nucleic acids. Substituents on the porphyrins that would be particularly useful in this regard include known DNA intercalating molecules and nucleic acid oligomers.

The chemoresponsive dye may be, for example, a pH sensitive dye. Dyes that are pH sensitive include pH indicator or acid-base indicator dyes that may change color upon exposure to acids or bases. Examples of pH sensitive dyes include Brønsted acid dyes. A Brønsted acid dye is a proton donor that can donate a proton to a Brønsted base (i.e., a proton acceptor), resulting in a change in spectral properties. Under certain pH conditions, a Brønsted acid dye may be a Brønsted base.

Examples of Brønsted acid dyes include protonated, but non-metalated, porphyrins; chlorines; bispocket porphyrins; phthalocyanines; and related polypyrrolic dyes. Examples of non-metalated porphyrin Brønsted acid dyes include 5,10, 15,20-tetrakis(2',6'-bis(dimethyl-t-butylsiloxyl)phenyl)porphyrin dication; 5,10,15,20-Tetraphenyl-21H,23H-porphyrin; or 5,10,15,20-Tetraphenylporphyrin dication. Other examples of Brønsted acid dyes include Chlorophenol Red, Bromocresol Green, Bromocresol Purple, Bromothymol Blue, Bromopyrogallol Red, Pyrocatechol Violet, Phenol Red, Thymol Blue, Cresol Red, Alizarin, Mordant Orange, Methyl Orange, Methyl Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange #25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, Malachite Green Carbinol Base, Nile Red, Nile Blue, Nitrazine Yellow, Bromophenol Red, Bromophenol Blue, Bromoxylenol Blue, Xylenol Orange Tetrasodium Salt, 1-[4-[[4-(dimethylamino)phenyl]azo]phenyl]-2,2,2-trifluoroethanone, 4-[2-[4-(dimethylamino)phenyl]ethenyl]-2,6-dimethyl-pyrylium perchlorate, and 1-amino-4-(4-decylphenylazo)-naphthalene.

The chemoresponsive dye may be, for example, a solvatochromic dye or a vapochromic dye. Solvatochromic dyes may change color depending upon the local polarity of their liquid micro-environment. Vapochromic dyes may change color depending upon the local polarity of their gaseous micro-environment. Most dyes are solvatochromic and/or vapochromic to some extent; however, some are much more responsive than others, especially those that can have strong dipole-dipole interactions. Examples of solvatochromic dyes include Reichardt's Dyes, Nile Red, Fluorescein, and polypyrrolic dyes.

An array that includes a pH sensitive dye and/or a solvatochromic or vapochromic dye may be useful in differentiating analytes that do not bind to, or bind only weakly to, metal ions. Such analytes include acidic compounds, such as carboxylic acids, and certain organic compounds lacking ligatable functionality. Examples of organic compounds lacking ligatable functionality include simple alkanes, arenes, and some alkenes and alkynes, especially if sterically hindered. Examples of organic compounds lacking ligatable functionality also include molecules that are sufficiently sterically hindered to preclude effective ligation. Arrays that include a pH sensitive and/or a solvatochromic or vapochromic dye are described, for example, in U.S. Patent Application Publication No. 2003/0143112 A1 to Suslick et al.

The chemoresponsive dye may be, for example, a redox sensitive dye that undergoes a change in spectral properties depending upon its oxidation state. Examples of dyes that are redox sensitive include redox indicators are disclosed in H. A. Laitinen, *Chemical Analysis* (McGraw-Hill: New York, 1960). Examples of redox indicators include methylene blue, naphthol blue-black, brilliant ponceau, α-naphthoflavone, basic fuchsin, quinoline yellow, thionin acetate, methyl orange, neutral red, diphenylamine, diphenylaminesulfonic acid, 1,10-phenanthroline iron(II), permanganate salts, silver salts, and mercuric salts.

The chemoresponsive dye may be, for example, a metal ion sensitive dye that undergoes a change in spectral properties in the presence of metal ions. Examples of dyes that are metal ion sensitive include metal ion indicators are disclosed in Laitinen [30]. Examples of metal ion indicator dyes include eriochrome black T, murexide, 1-(2-pyridylazo)-2naphthol, and pyrocatechol violet.

The chemoresponsive colorant may be a chemoresponsive pigment. Preferably the chemoresponsive pigment is a porous pigment. A porous pigment particle has a chemoresponsive surface area that is much greater than the chemoresponsive surface area of a corresponding nonporous pigment particle. Examples of porous pigments include porous calcium carbonate, porous magnesium carbonate, porous silica, porous alumina, porous titania, and zeolites.

The chemoresponsive colorant may be a chemoresponsive nanoparticle. A chemoresponsive nanoparticle may be a discrete nanoparticle, or it may be formed from nanoparticle-forming ions or molecules. Examples of nanoparticle-forming ions or molecules are disclosed in Murphy et al. [31]. The nanoparticle may be in a variety of forms, including a nanosphere, a nanorod, a nanofiber, and a nanotube. Examples of chemoresponsive nanoparticles include nanoporous porphyrin solids, semiconductor nanoparticles such as quantum dots, and metal nanoparticles. Examples of nanoporous porphyrin solids are disclosed in Suslick et al. [32].

A colorimetric array may further include a plurality of additional spots on the substrate, where each additional spot independently includes a chemoresponsive colorant. At least one spot of the additional spots may include an additional nanoporous pigment that is different from the first and second nanoporous pigments. An additional nanoporous pigment includes a nanoporous material and an immobilized, chemoresponsive colorant. The nanoporous material and the colorant may be as described above for nanoporous materials and chemoresponsive colorants. Preferably, each additional spot independently includes an additional nanoporous pigment that is different from the first and second nanoporous pigments. More preferably, each additional spot independently includes an additional nanoporous pigment, each of the additional nanoporous pigments is different, and each of the additional nanoporous pigments is different from the first and second nanoporous pigments. As noted above, two nanoporous pigments are different if their component nanoporous materials and/or their immobilized, chemoresponsive colorants are different.

A colorimetric array that further includes a plurality of additional spots on the substrate may include at least one spot that does not include a nanoporous pigment. For example, the array may include at least one spot including a chemoresponsive colorant that is not immobilized with a nanoporous material. Colorimetric arrays in which the spots do not include nanoporous pigments are disclosed, for example in U.S. Pat. Nos. 6,368,558 and 6,495,102 to Suslick et al., and in U.S. Patent Application Publication Nos. 2003/0143112, 2003/0129085 and 2003/0166298 to Suslick et al. [18-23]. Thus, a single colorimetric array may include spots including nanoporous pigments, and also may include spots that include only chemoresponsive colorants that are not immobilized with a nanoporous material.

The use of more than one type of chemoresponsive colorant may expand the range of analytes to which the array is sensitive, may improve sensitivity to some analytes, and/or may increase the ability to discriminate between analytes. In one example, a colorimetric array includes from 2 to 1,000 spots. Preferably a colorimetric array includes from 4 to 500 spots. More preferably, a colorimetric array includes from 8 to 250 spots. More preferably, a colorimetric array includes from 10 to 100 spots. More preferably, a colorimetric array includes from 16 to 49 spots, including from 36 spots. Each spot in a colorimetric array may include a different colorant. However, it may be desirable to include duplicate spots that include the same colorant. Duplicate spots may be useful, for example, to provide redundancy to the array and/or to serve as an indicator for quality control.

A method of making a colorimetric array includes depositing a first liquid at a first point on a substrate, depositing a second liquid at a second point on a substrate, converting the first liquid into a first spot on the substrate, and converting the second liquid into a second spot on the substrate. The first spot includes a first nanoporous pigment including a first nanoporous material and a first immobilized, chemoresponsive colorant. The second spot includes a second nanoporous pigment including a second nanoporous material and a second immobilized, chemoresponsive colorant. The second nanoporous pigment is different from the first nanoporous pigment.

In a first example, the first liquid includes a first nanoporous material precursor and a first chemoresponsive colorant. A nanoporous material precursor is a substance that will form a nanoporous material when it is solidified. In this example, converting the first liquid into a first spot includes solidifying the first nanoporous material precursor to form the first nanoporous material. The first nanoporous material precursor may be, for example, a polymer, a prepolymer, ceramic precursors, or mixtures of these. The first liquid may include other ingredients, such as a solvent and/or a surfactant.

The first nanoporous material precursor may include starting materials for a ceramic that have been at least partially hydrolyzed. The first liquid may be formed by combining ingredients including starting materials for a ceramic, a solvent, and the first chemoresponsive colorant to form a first mixture, and then hydrolyzing the first mixture to form a sol. Solidifying the first nanoporous material precursor may include condensing the first nanoporous material precursor to form a gel, and drying the gel to form the first nanoporous material.

The solidifying may include any method that converts the nanoporous material precursor into a nanoporous material. Examples of solidification methods include chemical cross-linking, exposure to UV radiation, and heating. In one example, the solidifying includes heating the liquid on the substrate. Initial curing at room temperature for 24 to 72 hours may be preferred in order to maintain porosity of the nanoporous pigment. Additional heating may be performed, for example, in a standard convection oven. If the substrate is temperature-sensitive, heating the liquid for 24 hours at temperatures lower than 70° C. is preferred. When preparing a spot that includes a nanoporous ceramic and a pH responsive dye as the chemoresponsive colorant, solidifying at 60° C. or even at room temperature is preferred. With more thermally robust substrates, solidifying may be completed much more rapidly, for example in 1 hour at 120° C.

The second liquid may be as described for the first liquid, and may be converted into the second spot in a similar way. For example, the second liquid may include a second nanoporous material precursor and a second chemoresponsive colorant, and converting the second liquid into a second spot may include solidifying the second nanoporous material precursor to form the second nanoporous material. The second nanoporous material precursor may be as described for the first nanoporous material precursor. Alternatively, the second liquid may include a colloidal suspension that is converted into a second spot by drying, as described below.

FIG. 1 is a schematic diagram, the top pathway of which is an example of this method. In this pathway, an initial liquid is formed by combining silica precursors, a chemoresponsive colorant, and a solvent including water. The liquid undergoes hydrolysis to form a colloidal sol, and is then deposited at a point on a substrate. The silica precursors are solidified by condensation to form a silica gel, followed by drying the gel to form a silica aerogel. The spot formed is thus the nanoporous aerogel including the immobilized, chemoresponsive colorant.

In a second example, the first liquid includes a first colloidal suspension including a first solvent and particles of the first nanoporous pigment. In this example, converting the first liquid into a first spot includes drying the first colloidal suspension. The first liquid may be formed by dispersing the particles of the first nanoporous pigment in the first solvent. The first liquid may include other ingredients, such as a surfactant.

The particles of the first nanoporous pigment may be formed by combining ingredients including starting materials for a ceramic, a second solvent, and the first chemoresponsive colorant to form a first mixture; hydrolyzing the first mixture to form a sol; and condensing the sol to form a second mixture including the particles of the first nanoporous pigment.

The second liquid may be as described for the first liquid, and may be converted into the second spot in a similar way. For example, the second liquid may include a second colloidal suspension including a third solvent and particles of the second nanoporous pigment, and converting the second liquid into a second spot may include drying the second colloidal suspension. The second liquid may be formed by dispersing the particles of the second nanoporous pigment in the third solvent. The particles of the second nanoporous pigment may be as described for the particles of the first nanoporous pigment.

Referring to FIG. 1, the bottom pathway is an example of this method. In this pathway, an initial liquid is formed by combining silica precursors, a chemoresponsive colorant, and a solvent including water. The preliminary liquid undergoes hydrolysis to form a colloidal sol, and then undergoes condensation and precipitation to form nanoporous pigment particles that include the chemoresponsive colorant in an immobilized state. A liquid is then formed by dispersing the nanoporous pigment particles and a surfactant in a solvent. This liquid is deposited at a point on a substrate, and then dried to form a silica aerogel. The spot formed is thus the aerogel including the chemoresponsive colorant.

In the method of forming a colorimetric array, the first and second liquids, and mixtures used to form the liquids, independently may include a solvent. Examples of solvents include 1,2-dichlorobenze, diglyme, methanol, 2-methoxyethanol, propylene glycol methyl ether acetate, water, and mixtures of these. Preferably the liquids include a solvent that contains a mixture of water and another solvent.

In the method of forming a colorimetric array, the first and second liquids, and mixtures used to form the liquids, independently may include a surfactant. A surfactant may be useful to enhance the solubility or dispersibility of the chemoresponsive colorant in a liquid, to improve flow control, to enhance the uniformity of the printing or of the color (i.e., "leveling"), and/or to improve wetting of the surface being printed (i.e., "wet-out"). The surfactant may be cationic, anionic, zwitterionic, or nonionic. Examples of surfactants include sodium dodecyl sulfate (SDS) and Triton X-100, a GE™ Silwet™ silicone surfactant, a 3M™ Novec™ fluorosurfactant, and mixtures of these.

Examples of starting materials for a ceramic include starting materials for materials such as hydroxyapatite, titanium oxide, lead zirconate, titanate, alumina, silica, zirconia, silicon nitride, barium titanate, and silicon carbide, or mixtures of these. In one example, starting materials for a silica ceramic may include at least one alkoxysilanes or halosilanes, and including a condensation catalyst. The alkoxysilane or halosilane may be, for example, tetramethoxysilane (TMOS), tetrachlorosilane (TCS), methyltrimethoxysilane (MTMS), methyltrichlorosilane (MTCS), octyltrimethoxysilane (OTES), phenethyltrimethoxysilane (PTMS), or mixtures of these. The condensation catalyst may be, for example, an acid such as hydrochloric acid (HCl) or nitric acid ($HNO_3$), or a base such as ammonium hydroxide ($NH_4OH$) or sodium hydroxide (NaOH), dissolved in water.

In a specific example, an initial mixture includes 5 to 50% by volume alkoxysilanes, 0.001 to 0.1 M hydrochloric acid as a condensation catalyst, a chemoresponsive colorant, 5 to 20% by volume water, 1 to 80% by volume solvents, and 0.01 to 2% by weight surfactant. This initial mixture may be hydrolyzed to form a sol, deposited on a substrate, condensed to form a gel, and dried to form a spot of an array. Alternatively, this initial mixture may be hydrolyzed to form a sol, and condensed to form a mixture that includes particles of a nanoporous pigment. These particles may then be dispersed in a solvent, deposited on a substrate, and dried to form a spot of an array.

Figure 2:
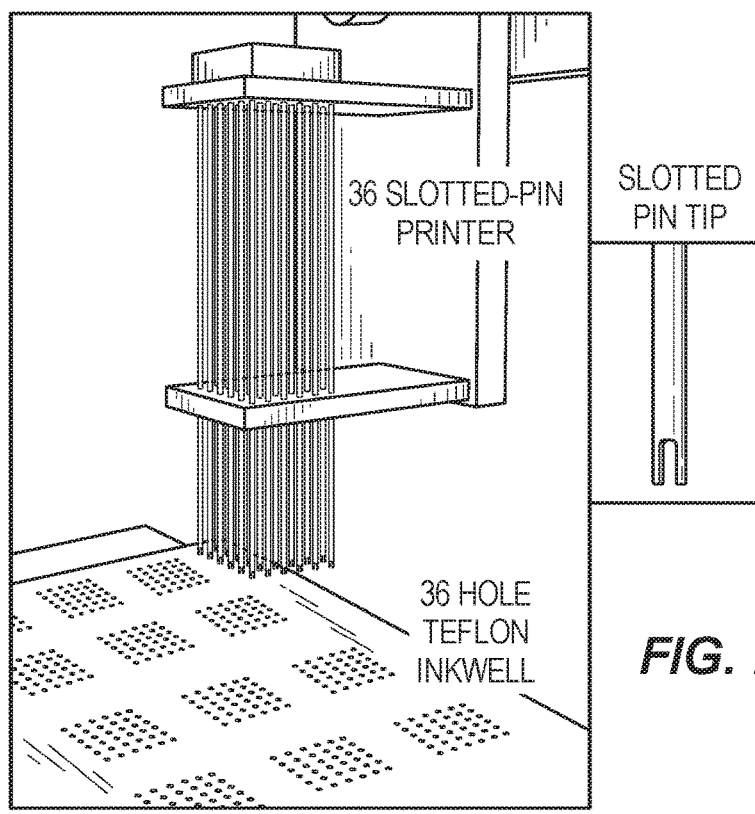
FIG. 2 is a set of images of a slotted dip-pin printer for depositing liquids on a substrate.

The depositing may include one or more printing techniques such as ink-jet, stamping and dip-pin printing. FIG. 2 is a set of images of a slotted dip-pin printer for depositing liquids on a substrate. Each of the liquids may be deposited on a single substrate. Alternatively, different liquids may be printed on different substrates, and the individual substrates then assembled together to form the array.

A method of making a colorimetric array may further include depositing a plurality of additional liquids at additional points on the substrate, and converting the additional liquids into a plurality of additional spots. Each additional spot independently includes a chemoresponsive colorant. At least one of the additional spots may include an additional nanoporous pigment that is different from the first and second nanoporous pigments. An additional nanoporous pigment includes a nanoporous material and an immobilized, chemoresponsive colorant. The nanoporous material and the colorant may be as described above for nanoporous materials and chemoresponsive colorants. Preferably, each additional spot independently includes an additional nanoporous pigment that is different from the first and second nanoporous pigments. More preferably, each additional spot independently includes an additional nanoporous pigment, each of the additional nanoporous pigments is different, and each of the additional nanoporous pigments is different from the first and second nanoporous pigments. As noted above, two nanoporous pigments are different if their component nanoporous materials and/or their immobilized, chemoresponsive colorants are different.

The method may include depositing from 2 to 1,000 liquids. Preferably the method includes depositing from 4 to 500 liquids. More preferably, the method includes depositing from 8 to 250 liquids. More preferably, the method includes depositing from 10 to 100 liquids. More preferably, the method includes depositing from 16 to 72 liquids, including from 24 to 36 liquids. Each liquid may include a different colorant. However, it may be desirable to include duplicate liquids that include the same colorant, as noted above.

A colorimetric array that includes first and second spots, each including a different nanoporous pigment, may be used for chemical analyses of gaseous and liquid analytes. A method of detecting an analyte in a sample includes obtaining a first image of the array in the absence of the analyte, obtaining a second image of the array in the presence of the sample, and analyzing a difference between the first image and the second image. The array may be used to detect a wide variety of analytes, regardless of the physical form of the analytes. The array may be used to detect any vapor emitting substance, including liquid, solid, or gaseous substances, and even when mixed with other vapor emitting substances. The array may be used to detect analytes dissolved in a solvent, including analytes in water. The array may be used to detect ionic or molecular analytes in a solvent, even when mixed with other dissolved analytes.

Obtaining an image of a colorimetric assay can be performed with any suitable imaging device. Examples of imaging devices include flatbed scanners, digital cameras (preferably with either constant illumination or reproducible flash intensity), CCD or CMOS video cameras (also preferably with reproducible illumination such as LED, white or tricolor). A handheld device can be constructed to read the internal sensor array with internal computing capability (for example a pocket PC or an embedded microprocessor), a light source and an imaging camera.

For gas or vapor analytes, a gas stream containing the analyte is passed over the array, and images may be obtained before, during and/or after exposure to the gas stream. Preferably an image is obtained after the sample and the array have equilibrated. If the gas stream is not pressurized, it may be useful to use a miniaturized pump.

For analytes dissolved in a solvent, either aqueous or non-aqueous, the first image may be obtained in air or, preferably, after exposure to the pure carrier solvent that is used of the sample. The second image of the array may be obtained after the start of the exposure of the array to the sample. Preferably an image is obtained after the sample and the array have equilibrated.

Analyzing the differences between the first image and the second image may include quantitative comparison of the digital images before and after exposure to the analyte. Using customized software such as ChemEye™ (Chem-Sensing, Champaign, Ill.) or standard graphics software such as Adobe® PhotoShop®, a difference map can be obtained by subtracting the first image from the second image. To avoid subtraction artifacts at the periphery of the spots, the center of each spot can be averaged.

Figures 3A, 3B, 3C:
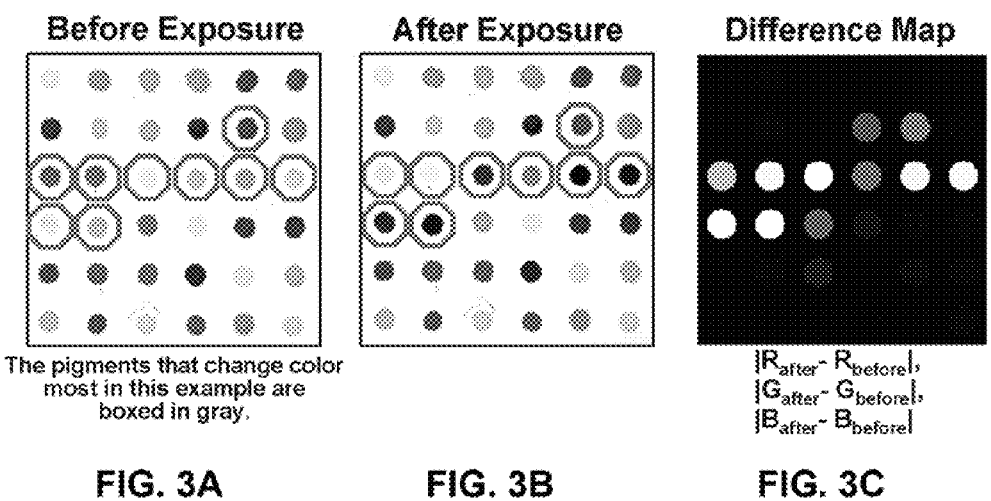
FIGS. 3A-3C are images from a calorimetric array, showing the array before exposure to a sample (3A), after exposure to a sample (3B), and a difference map of these two images (3C).

FIGS. 3A-3C are images from a colorimetric array, showing the array before exposure to a sample (3A), after exposure to a sample (3B), and a difference map of these two images (3C). The comparison data obtained from the difference map includes changes in red, green and blue values ($\Delta$RGB) for each spot in the array. Preferably the changes in spectral properties that occur upon exposure to an analyte, and the resultant color difference map, can serve as a unique fingerprint for any analyte or mixture of analytes at a given concentration.

In the simplest case, an analyte can be represented by a single 3x vector representing the $\Delta$RGB values for each colorant, where x is the number of colorants as set forth in equation (1). This assumes that equilibration is relatively rapid and that any irreversible reactions between analyte and colorant are slow relative to the initial equilibration time $$\text{Difference vector} = \Delta R1, \Delta G1, \Delta B1, \Delta R2, \Delta G2, \Delta B2, \ldots \Delta Rx, \Delta Gx, \Delta Bx \quad (1)$$

Alternatively, the temporal response of the analyte can be used to make rapid identification, preferably using a "time-stack vector" of $\Delta$RGB values as a function of time. In equation 2, a time-stack vector is shown for an array of 36 colorants at times m, n, and finally z, all using the initial scan as the baseline for the differences in red, green and blue values:

$$\begin{aligned}\text{Time stack vector} = &\Delta R1m, \Delta G1m, \Delta B1m, \Delta R2m,\\ &\Delta G2m, \Delta B2m, \Delta R36\ m, \Delta G36m, \Delta B36m, \ldots\\ &\Delta R1n, \Delta G1n, \Delta B1n, \ldots \Delta R36m, \Delta G36m,\\ &\Delta B36m, \ldots \Delta R36z, \Delta G36z, \Delta B36z\end{aligned} \quad (2)$$

Accordingly, each analyte response can be represented digitally as a vector of dimension 3xz, where x is the number of colorants and z is the number of scans at different times. Quantitative comparison of such difference vectors can be made simply by measuring the Euclidean distance in the 3xz space. Such vectors may then be treated by using routine chemometric or statistical analyses, including principal component analysis (PCA), hierarchical cluster analysis (HCA) and linear discriminant analysis. Statistical methods suitable for high dimensionality data are preferred. As an example, HCA systematically examines the distance between the vectors that represent each colorant, forming clusters on the basis of the multivariate distances between the analyte responses in the multidimensional $\Delta$RGB color space using the minimum variance ("Ward's") method for classification [33]. A dendrogram can then be generated that shows the clustering of the data from the Euclidean distances between and among the analyte vectors, much like an ancestral tree.

A method of detecting an analyte may include forming a derivative of the analyte of interest. This may be useful when the original analytes prove relatively non-responsive to the array colorants. In this case, a chemical reaction of the analyte may form one or more products that are well detected by the array colorants.

In one example, the response of arrays to various sugars dissolved in water may not be sufficient for direct analysis. However, the reaction of sugar analytes with boronic or boric acids yields secondary analytes that can be analyzed on an array. Without being bound to any particular theory, it appears that this may be ascribed to the fact that different carbohydrates have different association constants to boronic acid, leading to changes in solution pH [34-37].

In another example, an analyte may be partially oxidized prior to obtaining the second image of the colorimetric array. Partial oxidation of an analyte means oxidation that does not convert all of the carbon atoms of the analytes completely to carbon dioxide. By partially oxidizing analytes, new mixtures of partially oxidized analytes are formed that may provide a unique analytical fingerprint for the presence of the parent analytes. Partial oxidation may include contacting the analyte with an oxidizing agent, such as oxygen gas, hydrogen peroxide, hypochlorite, chlorine dioxide, chlorine, and optionally may include contacting the analyte with an oxidation catalyst. Preferably the oxidizing source is present at a concentration or amount that is sufficient to result in forming an oxidized analyte, but that is below that needed to fully oxidize the parent analyte completely to carbon dioxide. Colorimetric analysis using an array, where the analyte is partially oxidized, is described, for example, in U.S. Patent Application Publication No. 2003/0166298 A1 to Suslick et al.

Partial oxidation may form a mixture of alcohols, aldehydes, ketones, carboxylic acids, carbon monoxide, and/or carbon dioxide. For example, a sample including a weakly-responsive analyte can be converted to at least one partially oxidized analyte that is more volatile. In one example, hexane can be partially oxidized to derivative analytes such as hexanoic acid, hexanol, hexanal, and $C_6$-ketones. The more volatile organic compounds typically have a stronger interaction with the array, and thus may provide stronger responses than the parent analytes.

A colorimetric array that includes first and second spots, each including a nanoporous material and a chemoresponsive colorant, may be used to detect ammonia or other analytes in exhaled breath. Detection of ammonia in exhaled breath can be useful in detecting the presence of a *Helicobacter* infection or for diagnosing liver or renal function. The colorimetric detection of ammonia in exhaled breath is described, for example, in U.S. Patent Application Publication No. 2005/0171449 A1, with inventors Suslick et al.

A colorimetric array may be placed in a clear plastic cartridge, and the cartridge may then be sealed to protect the array from the ambient environment. A gaseous or liquid sample can be introduced by injecting the sample into the cartridge. Alternatively, a colorimetric array may be formed on a substrate, and a cover may be attached to the substrate to form a sealed chamber that encloses the array and that includes an inlet port, and optionally an exit port. Cartridges for colorimetric arrays are disclosed in U.S. Provisional Patent Application No. 61/094,311, filed Sep. 4, 2008, entitled Cartridge For Colorimetric Sensor Arrays, with inventor Kenneth S. Suslick, which is incorporated herein by reference.

Colorimetric arrays that include first and second spots, each including a different nanoporous pigment, can have increased stability, sensitivity and selectivity toward analytes than conventional colorimetric arrays. The nanoporous pigments may be more stable than the colorants in conventional colorimetric arrays, since the colorants of the nanoporous pigments are site-isolated within a nanoporous material, protecting from intermolecular reactions that can occur to solubilized dyes in solution. Leaching of the colorant into an analyte liquid is also reduced or eliminated.

Nanoporous pigments may provide increased color intensity for a given spot in an array, since the loading of the colorant in the spot is not limited by its solubility. This increased color intensity can provide for improved sensor sensitivity, since the magnitude of the change in spectral properties in response to an analyte can be greater. Nanoporous pigment arrays also may have better sensitivity than conventional colorimetric dye arrays. One reason for this increased sensitivity may be that the nanoporous material acts as pre-concentrator.

The following examples are provided to illustrate one or more preferred embodiments of the invention. Numerous variations may be made to the following examples that lie within the scope of the invention.

EXAMPLES

Example 1: Formation of a Nanoporous Pigment Colorimetric Array for Detection, Identification and Quantification of VOCs and TICs A colorimetric array for the detection and identification of Volatile Organic Chemicals (VOCs) and Toxic Industrial Chemicals (TICs) was manufactured using a nanoporous material precursor and chemically responsive colorants. The nanoporous material precursor in this example was an organically modified silica (ORGAMOSIL) sol-gel solution that included 5 to 50% by volume alkoxysilanes, 5 to 20% by volume water, 1 to 80% by volume solvents, 0.001 to 0.1 M hydrochloric acid as a condensation catalyst, and 0.01 to 2% by weight surfactant. The stirred formulation was added to each of the colorants in Table 1, and the resulting mixtures were loaded into a Teflon block containing individual cylindrical wells (⅜" deep) for each mixture.

A floating slotted dip-pin printer capable of delivering approximately 100 mL was used to print the liquids onto the surface of a hydrophobic PVDF membrane. The slotted dip-pin array was dipped into the inkwell with the formulations filled in the corresponding inkwell holes. The pin array was then lifted and pressed on a suitable substrate, yielding a printed array. Once printed, the arrays were cured at room temperature for 48 hours.

TABLE 1

Chemoresponsive Colorants Used For Analysis of TICs

| Spot # | Name |
|---|---|
| 1 | 2,3,7,8,12,13,17,18-Octaethyl-21H,23H-porphine zinc(II) |
| 2 | 5,10,15,20-Tetraphenyl-21H,23H-porphine zinc |
| 3 | Zinc tetramesitylporphyrin |
| 4 | 5,10,15,20-Tetrakis(pentafluorophenyl)-21H,23H-porphine zinc |

TABLE 1-continued

Chemoresponsive Colorants Used For Analysis of TICs

| Spot # | Name |
|---|---|
| 5 | 5,10,15,20-Tetraphenyl-21H,23H-porphine maganese(III) chloride |
| 6 | 5,10,15,20-Tetrakis(pentafluorophenyl)-21H,23H-porphyrin iron(III) chloride |
| 7 | 5,10,15,20-Tetraphenyl-21H,23H-porphine cobalt(II) |
| 8 | 1-[4-[[4-(dimethylamino)phenyl]azo]phenyl]-2,2,2-trifluoroethanone |
| 9 | 4-[2-[4-(dimethylamino)phenyl]ethenyl]-2,6-dimethyl-pyrylium perchlorate |
| 10 | 1-Amino-4-(4-decylphenylazo)-naphthalene |
| 11 | Methyl Red + $Bu_4NOH$ |
| 12 | Phenol Red + $Bu_4NOH$ |
| 13 | Cresol Red + $Bu_4NOH$ |
| 14 | m-Cresol Purple + $Bu_4NOH$ |
| 15 | Thymol Blue + $Bu_4NOH$ |
| 16 | Alizarin + $Bu_4NOH$ |
| 17 | Basic Fuchsin + $Bu_4NOH$ |
| 18 | Crystal Violet |
| 19 | Bromocresol Green |
| 20 | Bromophenol Red |
| 21 | Bromothymol Blue |
| 22 | Naphthol Blue Black |
| 23 | Bromopyrogallol Red |
| 24 | Pyrocatechol Violet |
| 25 | Nile Red |
| 26 | Disperse Orange #25 |
| 27 | 4-(4-Nitrobenzyl)pyridine + N-Benzylaniline |
| 28 | $Bu_4NBr$ + Bromochlorophenol Blue |
| 29 | $ZnOAc_2$ + mCresol Purple + $Bu_4NOH$ |
| 30 | Basic Fuschin + Tosic acid |
| 31 | $LiNO_3$ + Cresol Red |
| 32 | $HgCl_2$ + Bromophenol Blue + $Bu_4NOH$ |
| 33 | $HgCl_2$ + Phenol Red + $Bu_4NOH$ |
| 34 | $Cu(NO_3)_2$ |
| 35 | $AgNO_3$ + Bromocresol Green |
| 36 | $AgNO_3$ + Phenol Red |

Example 2: Detection, Identification and Quantification of TICs

The prepared arrays of Example 1 were cut to size and placed in puncturable, sealed polyacrylic cartridges. Premixed certified gases of 16 individual TICs were diluted using digital mass flow controllers to their immediately dangerous to life or health (IDLH) concentration. For each array, the resulting gas stream was contacted with the array in its cartridge. The image of each array was acquired using a flatbed scanner (V200; EPSON, Long Beach, Calif.) before and during exposure to the TICs. Rapid equilibration occurred, and images for analysis were acquired after two minutes exposure. Upon exposure to the analyte, the arrays underwent reversible reactions that resulted in well defined color changes. The RGB values were obtained in a difference map by subtracting the before image from the after image. To eliminate the possibility of subtraction artifacts caused by acquisitions near the spot edge, only the spot centers were included in the calculation. Measurements were performed using Photoshop® or ChemEye™.

Figure 4:
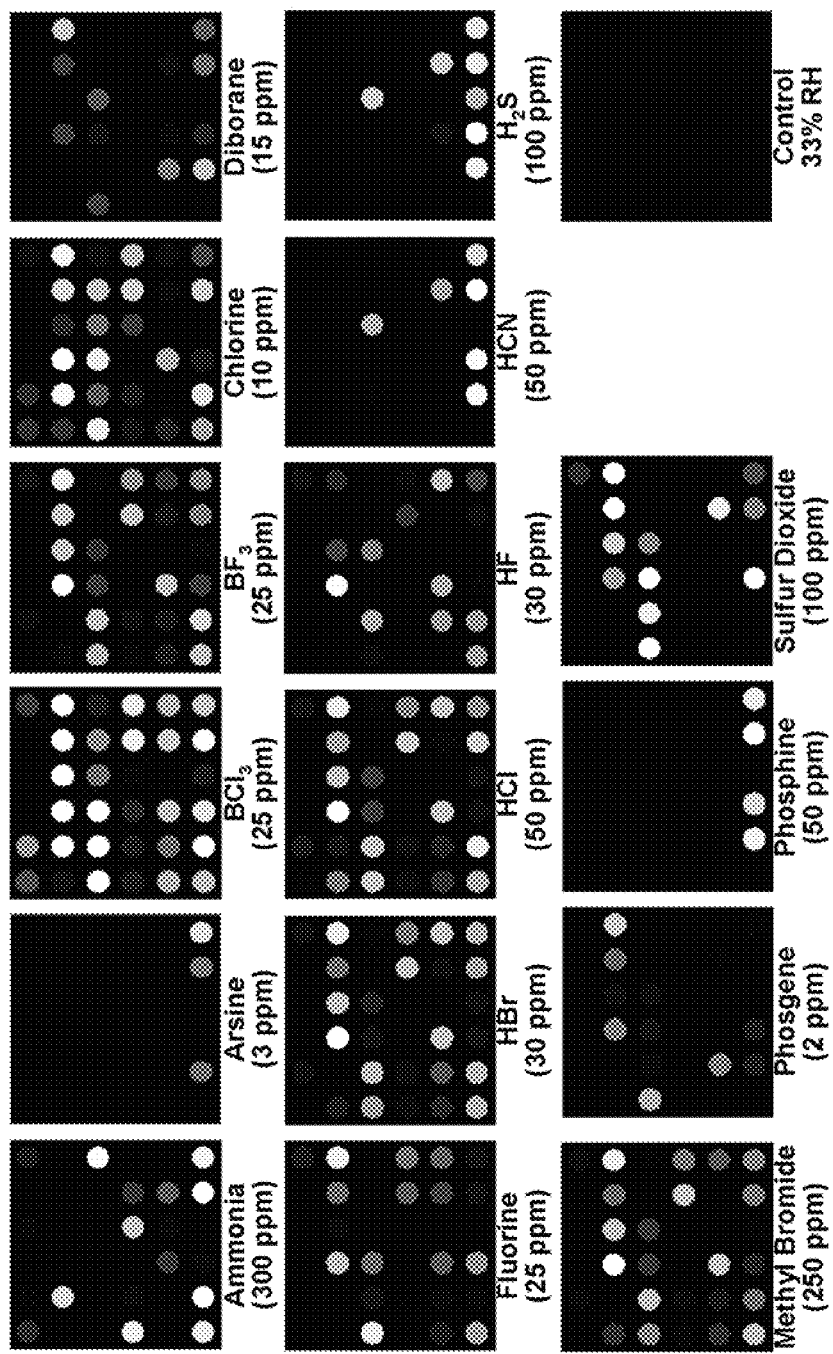
FIG. 4 is a set of color difference maps from calorimetric arrays after exposure to 16 different Toxic Industrial Chemicals (TICs) at their IDLH (immediately dangerous to life or health) concentrations.

A database was assembled from quintuplicate runs of the TICs at IDLH concentrations. Color change profiles, which were unique to each TIC, are shown in the color difference maps of FIG. 4.

Figure 5:
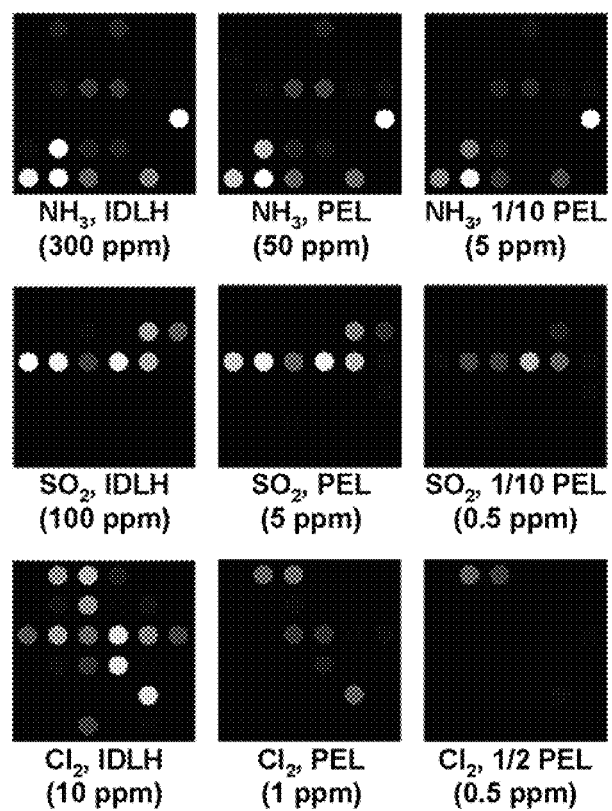
FIG. 5 is a set of color difference maps from colorimetric arrays after exposure to 3 different TICs at their IDLH concentrations, their PEL (permissible exposure level) concentrations, and well below their PEL concentrations.

Different concentrations of TICs were also determined with the colorimetric array. For purposes of illustration, three TICs (ammonia, sulfur dioxide, and chlorine) were chosen at concentrations corresponding to their respective IDLH, permissible exposure level (PEL), and sub-PEL concentrations, as listed in FIG. 5. Clearly identifiable differences in the color difference maps of FIG. 5 were obvious, even without statistical analysis.

Figure 6:
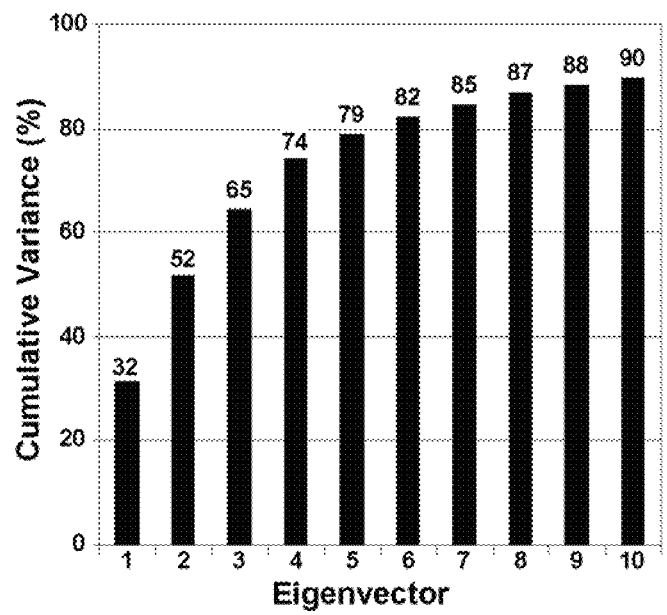
FIG. 6 is a graph of the results of a Principal Component Analysis (PCA) of the quintuplicate tests of a colorimetric array against 16 different TICs at their IDLH concentration.

For statistical analyses [33] of the changes in spectral properties, principal component analysis (PCA) and hierarchical clustering analysis (HCA) were used to analyze the color change profile database. PCA provides a quantitative evaluation of the analytical dispersion of a technique based on its number of independent dimensions of variance. Conventional electronic tongue sensors have shown only limited selectivity, which is believed to be due their relatively low number of independent dimensions. Typically, only two dimensions will account for more than 95% of total discrimination in these conventional sensors. In contrast, there was an extremely high level of dispersion with the colorimetric arrays of Example 1. When PCA was applied even to this family of very closely related analytes, there were 10 dimensions necessary for 90% of total discrimination, as indicated in the graph of FIG. 6.

Figure 7:
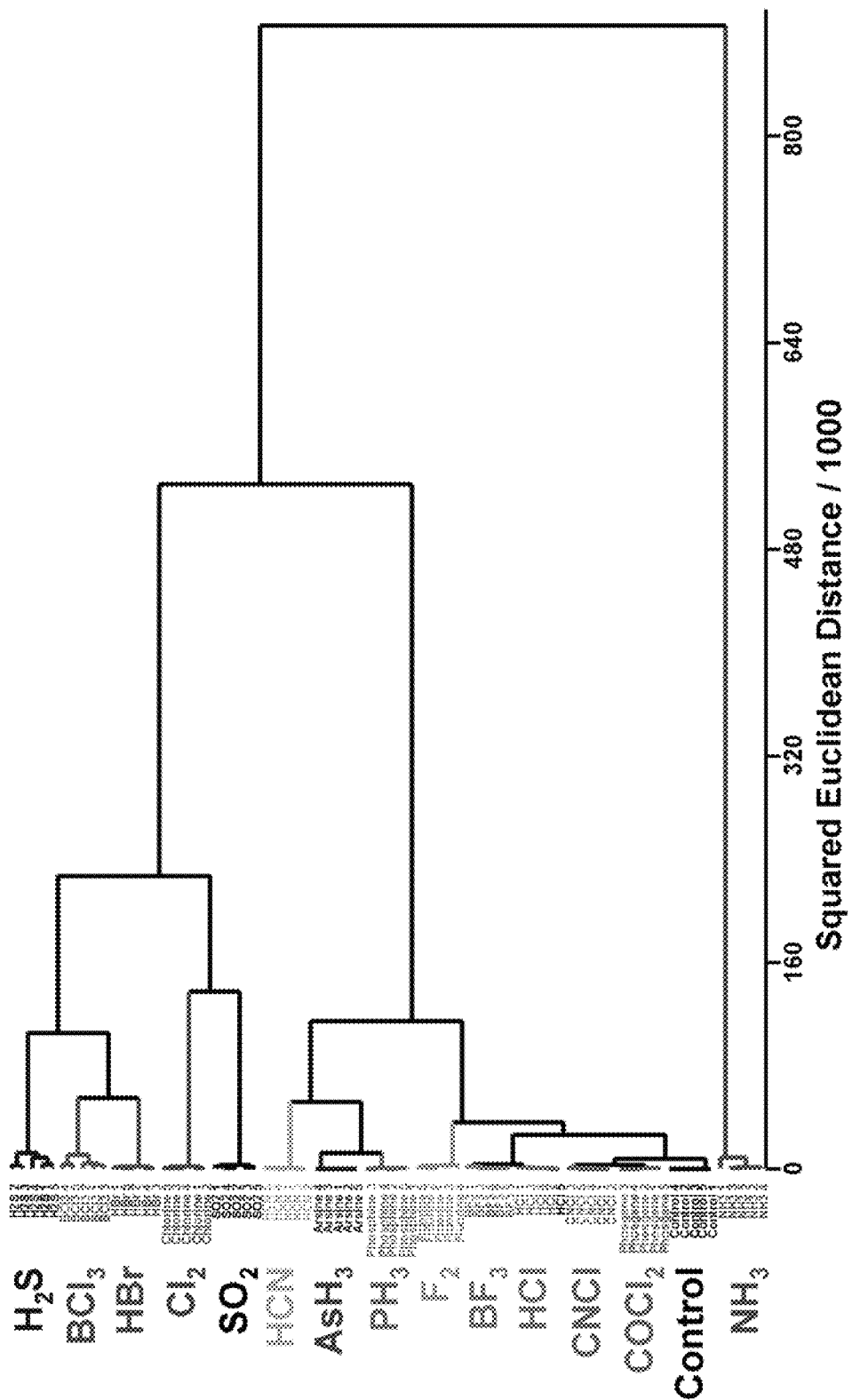
FIG. 7 illustrates a hierarchical cluster analysis of quintuplicate tests of a colorimetric array against 14 TICs, and a control sample.

FIG. 7 shows the dendrogram generated from the HCA analysis of the data for quintuplicate tests of 14 TICs at their IDLH, plus a control. Remarkably, all the TICs were accurately clustered with no errors or misclassifications out of 75 cases.

Example 3: Colorimetric Array for Detection and Identification of Carbohydrates

Tetramethylorthosilicate (TMOS), methyltrimethoxysilane (MTMS), methanol, and nano-pure water were combined in the molar ratio of 1:1:11:5. The mixture was stirred for 2 hours at room temperature. The stirred formulation was added to the chemoresponsive colorants listed in Table 2, and the mixtures were loaded into a block containing individual cylindrical wells having a depth of ⅜ inch for each mixture. A floating slotted dip-pin printer capable of delivering approximately 100 mL was used to print the liquids onto the surface of a nitrocellulose acetate hydrophilic membrane (MILLIPORE, Cat No. SSWP14250, 3.0 μm). The slotted dip-pin array was dipped into the inkwell with the formulations filled in the corresponding inkwell holes. The pin array was then lifted and pressed on a suitable substrate, yielding a printed array. Once printed, the arrays were cured at room temperature for 24 hours and then at 65° C. for 24 hours.

TABLE 2

Chemoresponsive Colorants used for Analysis of Sugars and Sweeteners

| Spot # | Name |
| --- | --- |
| 1 | Bromophenol Blue |
| 2 | Tetrabromophenol Blue |
| 3 | 3',3'',5',5''-tetraiodophenosulfonephthalein |
| 4 | Bromochlorophenol Blue |
| 5 | Bromocresol Green |
| 6 | Chlorophenol Red |
| 7 | Bromophenol Red |
| 8 | Bromocresol Purple |
| 9 | Bromoxylenol Blue |
| 10 | Phenol Red |
| 11 | m-Cresol Purple |
| 12 | Xylenol Orange tetrasodium salt |
| 13 | Bromopyrogallol Red |
| 14 | Methyl Yellow |
| 15 | Congo Red |
| 16 | Methyl Orange |

Example 4: Detection, Identification and Quantification of Sugars and Sweeteners The colorimetric arrays described in Example 3 were tested against 15 different sugars (including both mono- and di-saccharides), artificial sweeteners and sugar alcohols. The analytes were D-(−)-Fructose, D-(+)-Galactose, D-(+)-Glucose, β-Lactose, Maltitol, D-Mannitol, D-(+)-Mannose, D-(+)-Melibiose, L-Rhamnose, D-(−)-Ribose, Saccharin, Sorbitol, Sucrose, Xylitol, D-(+)-Xylose. Each analyte was dissolved in 1 mM phosphate buffer at pH 7.4, with 5 mM 3-nitrophenylboronic acid added. The concentration of each analyte except for sucrose was 25 mM, and the concentration of sucrose was 150 mM.

Figure 8:
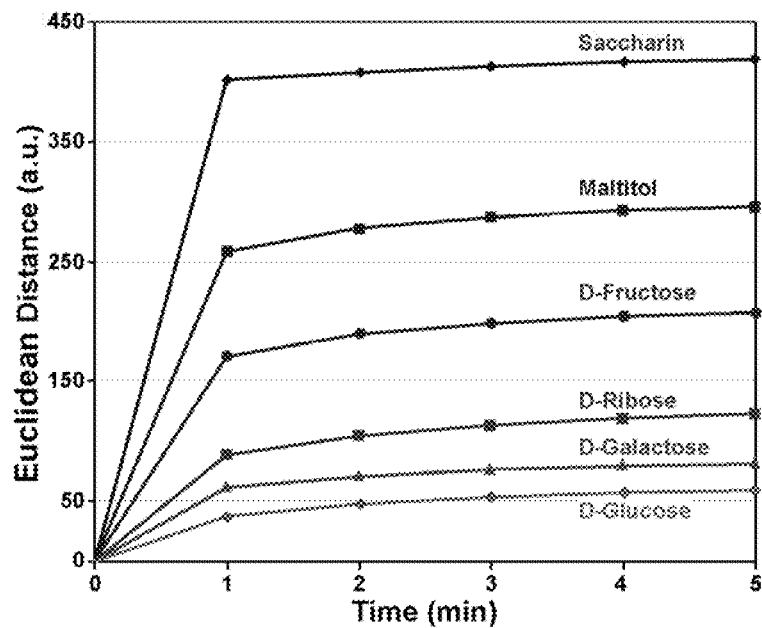
FIG. 8 is a graph of the response time of a calorimetric array to six different representative sugars or sweeteners at 25 mM, as represented by the change in Euclidean distance over time.

For each analyte, the array was placed in a puncturable cartridge, and the cartridge was placed atop an Epson V200 flatbed photo scanner. A first image was obtained with the array exposed to a blank buffer solution. The buffer solution was removed, and a sugar analyte solution was injected. After a 5 minute delay, the array was scanned again with the flatbed photo scanner. The delay ensured complete equilibration of the array, since 90% of the equilibration occurred in less than one minute. FIG. 8 is a graph of the response time of a colorimetric array to the sugars and sweeteners, as represented by the change in Euclidean distance over time.

Figure 9:
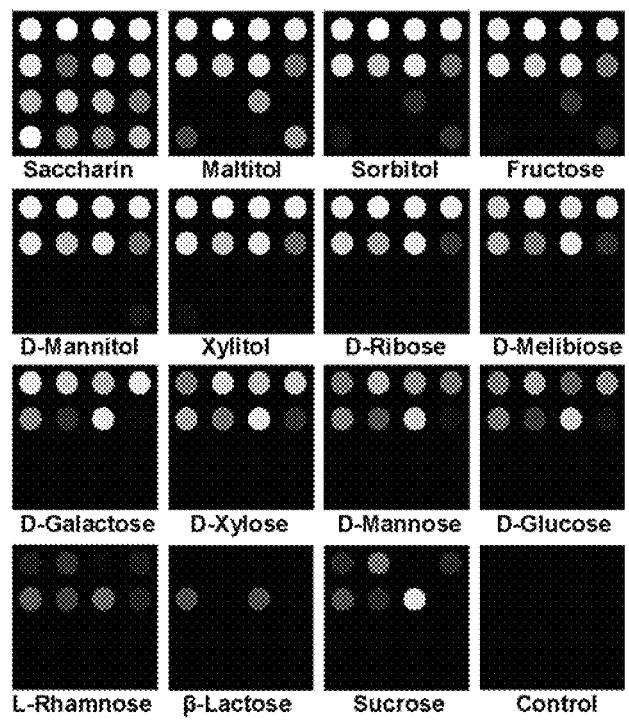
FIG. 9 is a set of color difference maps from calorimetric arrays after exposure to 14 sugars and sweeteners at 25 mM concentration, to sucrose at 150 mM concentration, and to a control.
Figure 10:
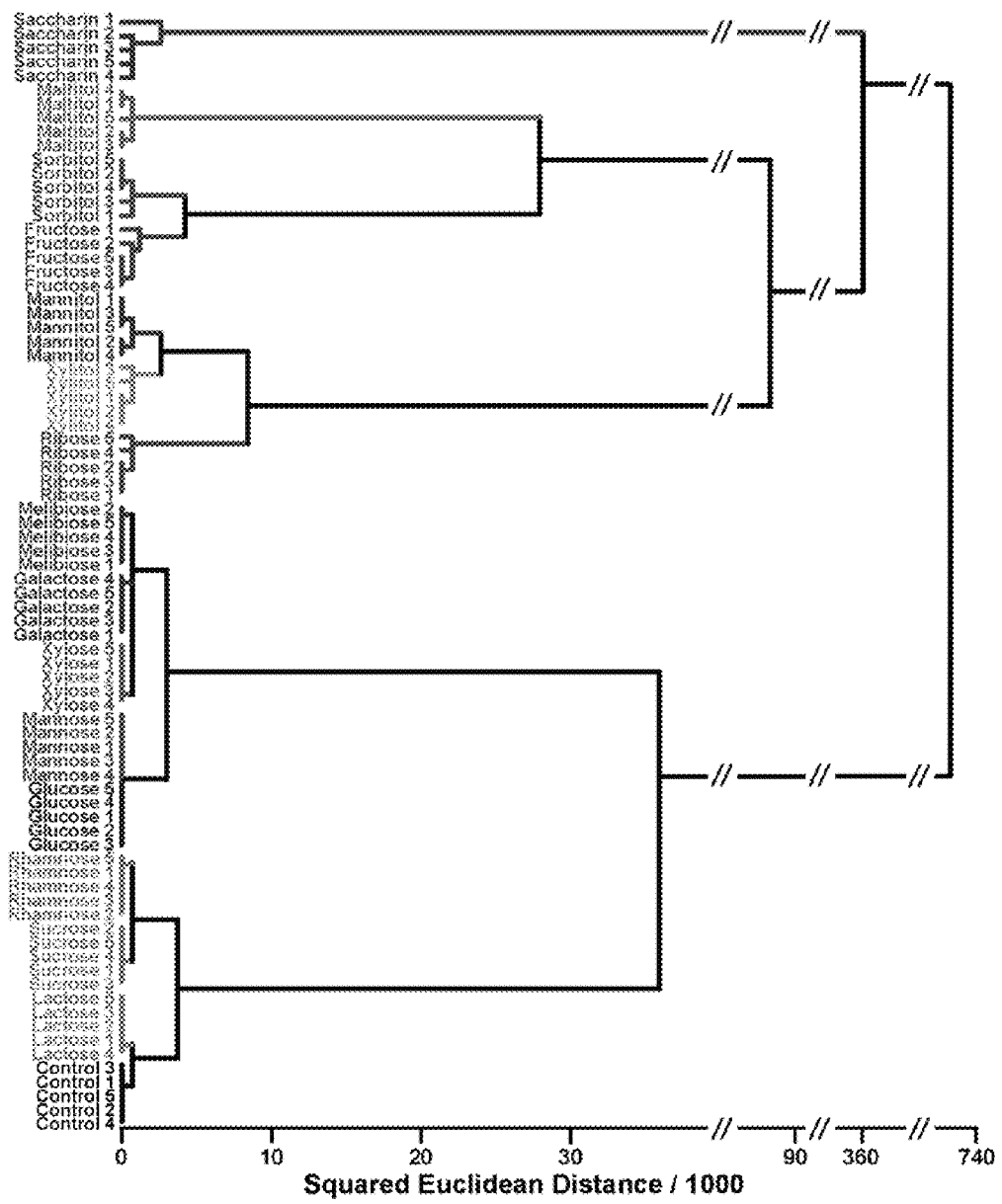
FIG. 10 illustrates a hierarchical cluster analysis for quintuplicate tests of the colorimetric array against the 15 sugars and sweeteners of FIG. 9, and a control.

Using the procedures of Example 2, difference maps were obtained for each analyte, a database was assembled from quintuplicate runs of the sugar analytes, and statistical analysis was performed. Color change profiles, which were unique to each analyte, are shown in the color difference maps of FIG. 9. FIG. 10 shows the HCA dendrogram generated from the HCA analysis of the data. Remarkably, all the carbohydrates were accurately identified and identified against one another with no errors or misclassifications out of 80 cases.

Example 5: D-Glucose Concentration Study

In addition to high discrimination, high sensitivity to carbohydrates is essential for most practical applications. For example, the physiological range of glucose concentrations is from about 2 mM to about 50 mM; normal fasting plasma glucose (FPG) is about 5 mM and the threshold of diabetes is above 7 mM. Also, diabetic glucose concentrations 2 hours after an oral glucose tolerance test are above 11.1 mM [38].

Figure 11:
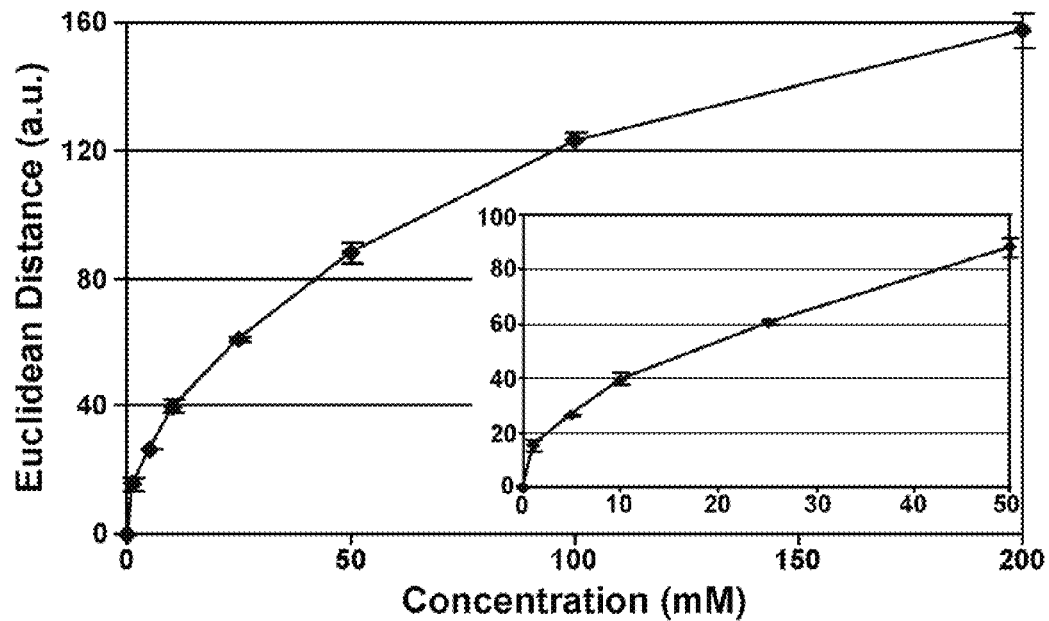
FIG. 11 is a graph of the total Euclidean distance of the change in spectral properties of a colorimetric array as a function of D-glucose concentration.

The limit of detection (LOD) of the colorimetric array of Example 3 was determined by contacting the arrays with samples containing concentrations of 1 mM, 5 mM, 10 mM, 25 mM, 50 mM, 100 mM, and 200 mM of D-glucose in a blank buffer solution. Concentration profiles were constructed by plotting the total Euclidean distance of the array color change against the D-Glucose concentration. The overall response of the array, as measured by the total Euclidean difference vs. D-glucose concentration is shown in FIG. 11. The lower limit of detection (LOD) of the array, defined as 3× signal to noise, was <1 mM.

Example 6: D-Glucose Cycling Experiment

Figure 12:
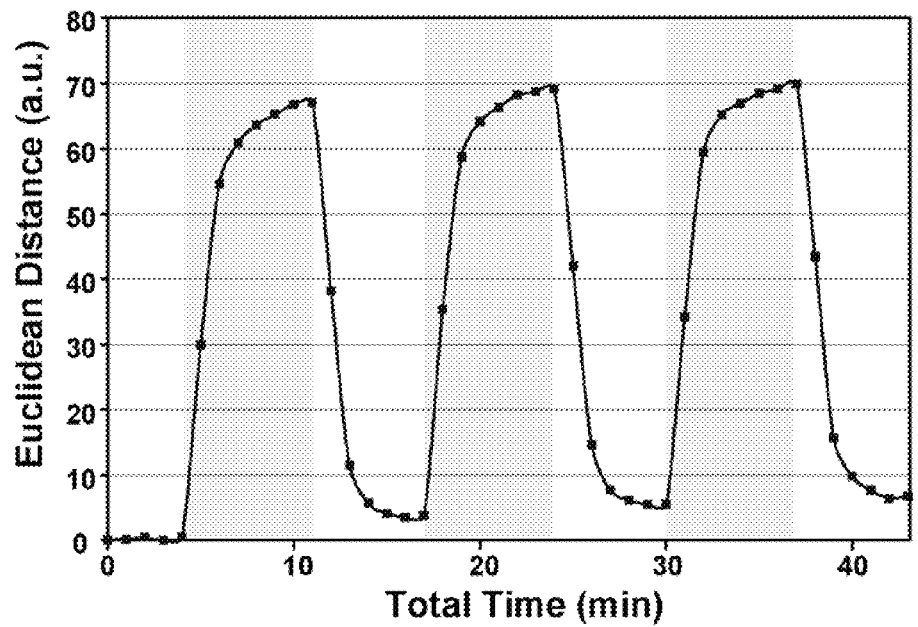
FIG. 12 is a graph of the change in Euclidean distance over time, during a repeated cycling of a colorimetric array between D-glucose (gray) and a buffer.

While the colorimetric arrays of Example 3 were inexpensive, disposable, and meant for single use, many of the reactions taking place were, in fact, reversible. Therefore, the reusability of the arrays was examined by exposing arrays to a blank buffer solution using a 20 ml/min flow system, obtaining a first image, and then cycling to the same buffer infused with 25 mM D-glucose, followed by plain buffer again. This process was repeated for three complete cycles. Due to dead volume and mixing times in the flow apparatus, full equilibration required approximately 6 minutes. The intrinsic response time of the array in the absence of the dead volume was less than 30 seconds. Surprisingly good reusability was observed, as shown in the graph of FIG. 12.

While various embodiments of the invention have been described, it will be apparent to those of ordinary skill in the art that other embodiments and implementations are possible within the scope of the invention. Accordingly, the invention is not to be restricted except in light of the attached claims and their equivalents.

REFERENCES

1. Gardner, J. W.; Bartlett, P. N. Electronic Noses: Principles and Applications; Oxford University Press: New York, 1999.
2. Albert, K. J.; Lewis, N. S.; Schauer, C. L.; Sotzing, G. A.; Stitzel, S. E.; Vaid, T. P.; Walt, D. R. Chem. Rev. 2000, 100, 2595.
3. Lewis, N. S. Accts. Chem. Res. 2004, 37, 663-672.
4. Johnson, B. A.; Leon M. J. Comp. Neurol. 2007, 503, 1-34.
5. Anslyn E. V. J. Org. Chem. 2007, 72, 687-699.
6. Anand, V.; Kataria, M.; Kukkar, V.; Saharan, V.; Choudhury, P. K. Drug Discovery Today 2007, 12, 257-265.
7. Toko, K. Biomimetic Sensor Technology; Cambridge University Press: Cambridge, UK, 2000.
8. Suslick, K. S.; Bailey, D. P.; Ingison, C. K.; Janzen, M.; Kosal, M. A.; McNamara III, W. B.; Rakow, N. A.; Sen, A.; Weaver, J. J.; Wilson, J. B.; Zhang, C.; Nakagaki, S. Quimica Nova 2007, 30, 677-681.
9. Suslick, K. S. MRS Bull. 2004, 29, 720-725.
10. Suslick, K. S.; Rakow, N. A.; Sen, A. Tetrahedron 2004, 60, 11133-11138.
11. Wang, J.; Luthey-Schulten, Z. A.; Suslick, K. S., Proc. Natl. Acad. Sci. U.S.A. 2003, 100, 3035-3039.
12. Rakow, N. A.; Suslick, K. S., Nature 2000, 406, 710-713.
13. Rakow, N. A.; Sen, A.; Janzen, M. C.; Ponder, J. B.; Suslick, K. S. Angew. Chem. Int. Ed. 2005, 44, 4528-4532.
14. Janzen, M. C.; Ponder, J. B.; Bailey, D. P.; Ingison, C. K.; Suslick, K. S. "Colorimetric Sensor Arrays for Volatile Organic Compounds" Anal. Chem. 2006, 78, 3591-3600.
15. Zhang, C.; Suslick, K. S., J. Am. Chem. Soc. 2005, 127, 11548-11549.
16. Zhang, C.; Bailey, D. P.; Suslick, K. S., J. Agric. Food Chem. 2006, 54, 4925-4931.
17. Zhang, C.; Suslick, K. S. J. Agric. Food Chem., 2007, 55, 237-242.
18. Suslick, K. S.; Rakow, N. A. "Colorimetric Artificial Nose Having an Array of Dyes and Method for Artificial Olfaction" U.S. Pat. No. 6,368,558; Apr. 9, 2002.
19. Suslick, K. S.; Rakow, N. A.; Sen, A. "Colorimetric Artificial Nose Having an Array of Dyes and Method for Artificial Olfaction: Shape Selective Sensors" U.S. Pat. No. 6,495,102 B1; Dec. 17, 2002.
20. Suslick, K. S.; Rakow, N. A.; Sen, A.; McNamara, W. B. III; Kosal, Margaret E. "Colorimetric artificial nose having an array of dyes and method for artificial olfaction" U.S. Patent Appl. 20030143112; Jul. 21, 2003.
21. Suslick, K. S.; Rakow, N. A.; Sen, A. "Siloxy porpyhrins and metal complexes thereof" U.S. Patent Appl. 20030129085; Jul. 10, 2003.
22. Suslick, K. S. "Colorimetric artificial nose having an array of dyes and method for artificial olfaction" U.S. Patent Appl. 20030166298; Sep. 4, 2003.
23. Suslick, K. S.; Rakow, N. A.; Sen, A.; McNamara, W. B. III; Kosal, Margare E. "Colorimetric Artificial Nose having an Array of Dyes and Method for Artificial Olfaction" U.S. Pat. No. 7,261,857; Aug. 28, 2007.
24. Zaggout, F. R., J. Dispersion Sci. Technol. 2005, 26, 757-761.
25. Rottman, C.; Ottolenghi, M.; Zusman, R.; Lev, O.; Smith, M.; Gong, G.; Kagan, M. L.; Avnir, D., Mater. Lett. 1992, 13, 293-298.
26. Zusman, R.; Rottman, C.; Ottolenghi, M.; Avnir, D., J. Non-Cryst. Solids 1990, 122, 107-109.
27. Kowada, Y.; Ozeki, T.; Minami, T., J. Sol-Gel Sci. Technol. 2005, 33, 175-185.
28. Zaggout, F. R.; El-Nahhal, I. M.; Qaraman, A. E.-F. A.; Al Dahoudi, N., Mate. Lett. 2006, 60, 3463-3467.
29. Villegas, M. A.; Pascual, L., Thin Solid Films 1999, 351, 103-108.
30. Laitinen, H. A. *Chemical Analysis* (McGraw-Hill: New York, 1960)
31. Murphy, C. J. et al. Chem. Commun. 2008, 544-557.
32. Suslick, K. S. et al. Acc. Chem. Res. 2005, 38, 283-291.
33. Hasswell, S., Practical Guide To Chemometrics; Dekker: NY, 1992.
34. Lee, J. W.; Lee, J.-S.; Chang, Y.-T., Angew. Chem., Int. Ed. Engl. 2006, 45, 6485-6487.
35. Dowlut, M.; Hall, D. G., J. Am. Chem. Soc. 2006, 128, 4226-4227.
36. Yan, J.; Springsteen, G.; Deeter, S.; Wang, B., Tetrahedron 2004, 60, 11205-11209.
37. James, T. D.; Sandanayake Samankumara, K. R. A.; Shinkai, S., Angew. Chem., Int. Ed. Engl. 1996, 35, 1911-1922.
38. Larson, P. R.; Kronenberg, H. M.; Melmed, S.; Polonsky, K. S. (eds.) Williams Textbook of Endocrinology, 10th ed. Saunders: Philadelphia, 2003.

What is claimed is:

1. A colorimetric sensor array comprising:
   a substrate;
   a first spot on the substrate, comprising a first nanoporous pigment, the first nanoporous pigment comprising a first nanoporous material and a first immobilized, chemoresponsive colorant; and
   a second spot on the substrate, comprising a second nanoporous pigment, the second nanoporous pigment comprising a second nanoporous material and a second immobilized, chemoresponsive colorant;
   where the first nanoporous pigment differs from the second nanoporous pigment, and
   where the first and second nanoporous pigments are cross-reactive with one another with respect to at least one analyte,
   where the first immobilized, chemoresponsive colorant comprises a chemoresponsive pigment,
   where the chemoresponsive pigment is a porous pigment.

2. The colorimetric sensor array of claim 1, where the first immobilized, chemoresponsive colorant comprises a dye insolubilized by the first nanoporous material.

3. The colorimetric sensor array of claim 2, where the dye is selected from the group consisting of a Lewis acid-base dye, a structure sensitive porphyrin, a pH sensitive dye, a solvatochromic dye, a vapochromic dye, a redox sensitive dye, and a metal ion sensitive dye.

4. The colorimetric sensor array of claim 2, where the dye is a Lewis acid-base dye selected from the group consisting of a metal-ion containing dye, a boron-containing dye, a boronic acid containing dye, and a dye comprising an accessible heteroatom having a lone electron pair.

5. The colorimetric sensor array of claim 4, where the dye is a metal-ion containing dye selected from the group consisting of a metalloporphyrin, a salen complex, a chlorin, a bispocket porphyrin, and a phthalocyanine.

6. The colorimetric sensor array of claim 2, where the dye is a structure sensitive porphyrin selected from the group consisting of a tetrakis(2,4,6-trimethoxyphenyl)-porphyrin, a silylether-metalloporphyrin, and a siloxyl-substituted bispocket porphyrin.

7. The colorimetric sensor array of claim 2, where the dye is a pH sensitive dye selected from the group consisting of a Bronsted acid dye and a Bronsted base dye.

8. The colorimetric sensor array of claim 2, where the dye is responsive to at least one chemical interaction selected from the group consisting of Lewis acid-base interaction, Bronsted acid-base interaction, ligand binding, π-π complexation, hydrogen bonding, polarization, oxidation/reduction, and metal coordination.

9. The colorimetric sensor array of claim 1, where the first immobilized, chemoresponsive colorant comprises a chemoresponsive nanoparticle.

10. The colorimetric sensor array of claim 9, where the chemoresponsive nanoparticle is selected from the group consisting of a nanoporous porphyrin solid, a semiconductor nanoparticle, and a metal nanoparticle.

11. The colorimetric sensor array of claim 1, where the first and second nanoporous materials are the same, and the first and second immobilized, chemoresponsive colorants are different.

12. The colorimetric sensor array of claim 1, where the first and second nanoporous materials are different, and the first and second immobilized, chemoresponsive colorants are the same.

13. The colorimetric sensor array of claim 1, where the first and second nanoporous materials are different, and the first and second immobilized, chemoresponsive colorants are different.

14. The colorimetric sensor array of claim 1, further comprising a plurality of additional spots on the substrate, each spot of the plurality independently comprising a chemoresponsive colorant.

15. The colorimetric sensor array of claim 14, where at least one spot of the plurality comprises an additional nanoporous pigment, different from the first and second nanoporous pigments.

16. The colorimetric sensor array of claim 14, where each spot of the plurality independently comprises an additional nanoporous pigment, different from the first and second nanoporous pigments.

17. The colorimetric sensor array of claim 16, where each additional nanoporous pigment of the plurality is different.

18. The colorimetric sensor array of claim 1, further comprising an oxidizing source to pretreat the analyte gas stream before contact with the colorimetric sensor array.

19. The colorimetric sensor array of claim 18, wherein the oxidizing source comprises an oxidizing agent.

20. The colorimetric sensor array of claim 19, wherein the oxidizing agent is a solid oxidant.

21. The colorimetric sensor array of claim 19, further comprising an oxidation catalyst wherein the oxidation catalyst comprises a heterogeneous catalyst.

22. A colorimetric sensor array for determining the identity and concentration of an analyte, comprising:
a substrate; and
a plurality of nanoporous pigments on the substrate,
wherein each member of the plurality of nanoporous pigments comprises a nanoporous material and an immobilized, chemoresponsive colorant, provided that at least one member of the plurality of nanoporous pigments differs from another member of the plurality of nanoporous pigments,
wherein each member of the plurality of nanoporous pigments is cross-reactive with other members of the plurality of nanoporous pigments with respect to the analyte, and
wherein the colorimetric sensor array is configured to determine the identity and concentration of the analyte based upon a pattern of color change associated with interaction of the analyte with the plurality of nanoporous pigments,
where the immobilized, chemoresponsive colorant comprises a chemoresponsive pigment,
where the chemoresponsive pigment is a porous pigment.

23. A colorimetric sensor array for determining the identity and concentration of an analyte, comprising:
a substrate; and
a plurality of nanoporous pigments and chemoresponsive dyes on the substrate,
wherein each member of the plurality of nanoporous pigments comprises a nanoporous material and an immobilized, chemoresponsive colorant,
wherein at least one member of the plurality of nanoporous pigments and chemoresponsive dyes differs from another member of the plurality of nanoporous pigments and chemoresponsive dyes,
wherein each member of the plurality of nanoporous pigments and chemoresponsive dyes is cross-reactive with other members of the plurality of nanoporous pigments and chemoresponsive dyes with respect to the analyte, and
wherein the colorimetric sensor array is configured to determine the identity and concentration of the analyte based upon a pattern of color change associated with interaction of the analyte with the plurality of nanoporous pigments and chemoresponsive dyes,
where the immobilized, chemoresponsive colorant comprises a chemoresponsive pigment,
where the chemoresponsive pigment is a porous pigment.

24. The colorimetric sensor array of claim 1, wherein said colorimetric sensor array is configured to generate a color difference map, wherein the color difference map comprises changes in spectral properties that occur upon exposure of the at least one analyte to the first and second nanoporous pigments.

25. The colorimetric sensor array of claim 1, wherein the first and second nanoporous pigments are cross-reactive with one another with respect to greater than one analyte.

26. The colorimetric sensor array of claim 22, wherein said colorimetric sensor array is configured to generate a color difference map, wherein the color difference map comprises changes in spectral properties that occur upon exposure of the analyte to the plurality of nanoporous pigments.

27. The colorimetric sensor array of claim 22, wherein each member of the plurality of nanoporous pigments is cross-reactive with other members of the plurality of nanoporous pigments with respect to greater than one analyte.

28. The colorimetric sensor array of claim 23, wherein the colorimetric sensor array is configured to generate a color difference map, wherein the color difference map comprises the pattern of color change associated with interaction of the at least one analyte with the plurality of nanoporous pigments and chemoresponsive dyes.

29. The colorimetric sensor array of claim 23, wherein each member of the plurality of nanoporous pigments and chemoresponsive dyes is cross-reactive with other members of the plurality of nanoporous pigments and chemoresponsive dyes with respect to greater than one analyte.

* * * * *